US007208162B2

(12) United States Patent
Prince et al.

(10) Patent No.: US 7,208,162 B2
(45) Date of Patent: Apr. 24, 2007

(54) COMBINATION THERAPY OF RESPIRATORY DISEASES USING ANTIBODIES AND ANTI-INFLAMMATORY AGENTS

(75) Inventors: Gregory Prince, Potomac, MD (US); Leslie S. Johnson, Germantown, MD (US)

(73) Assignees: MedImmune, Inc., Gaithersburg, MD (US); Virion Systems, Inc., Rockville, MD (US)

( * ) Notice: Subject to any disclaimer, the term of this patent is extended or adjusted under 35 U.S.C. 154(b) by 605 days.

(21) Appl. No.: 09/848,377

(22) Filed: May 3, 2001

(65) Prior Publication Data

US 2002/0051787 A1 May 2, 2002

Related U.S. Application Data

(60) Provisional application No. 60/201,404, filed on May 3, 2000.

(51) Int. Cl.
*A61K 39/155* (2006.01)

(52) U.S. Cl. .............................. 424/211.1; 424/130.1; 424/133.1; 424/135.1; 424/141.1; 424/147.1; 424/164.1; 424/178.1

(58) Field of Classification Search ............. 424/147.1, 424/178.1, 130.1, 133.1, 135.1, 141.1, 164.1, 424/211.1
See application file for complete search history.

(56) References Cited

U.S. PATENT DOCUMENTS 5,290,540 A * 3/1994 Prince et al. ................. 424/45
5,824,307 A * 10/1998 Johnson .................... 424/133.1

FOREIGN PATENT DOCUMENTS

WO   WO 01/82966   11/2001

OTHER PUBLICATIONS

Johnson et al., The Journal of infectious Diseases, 180: 35-40, 1999.*
Smyth et al., Immunological responses to respiratory syncytial virus infection in infancy Arch Dis Child 1997 76: 210-214.*
Prince, G.A., "Respiratory Syncytial Virus Antiviral Agents", Expert Opinion on Therapeutic Patents, pp. 753-762, 9/6 (1999).
Ottolini, M.G., et al., "Prevention and Treatment Recommendations for Respiratory Syncytial Virus Infection Background and Clinical Experience 40 years after Discovery," in Drugs, 54/6, pp. 867-884, (1997).
Jiang, Zili, et al., "Autocrine Regulation and Experimental Modulation of Interleukin-6 Expression by Human Pulmonary Epithelial Cells Infected with Respiratory Syncytial Virus", Journal of Virology, vol. 72, No. 3, Mar. 1998, pp. 2496-2499.
Prince, Gregory, et al., "Treatment of Respiratory Syncytial Virus Bronchiolitis and Pneumonia in a Cotton Rat Model with Systemically Administered Monoclonal Antibody (Palivizumab) and Glucocorticosteroid", Journal of Infectious Diseases, vol. 182, No. 5, Nov. 2000, pp. 1326-1330.
Bulow et al., Prednisolone treatment of Respiratory Syncytial Virus Infection: a randomized controlled trial of 147 infants, *Pediatrics*, 104 (Dec. 6, 1999), p. e77).

* cited by examiner

*Primary Examiner*—Bruce R. Campell
*Assistant Examiner*—Myron G. Hill
(74) *Attorney, Agent, or Firm*—Elliot M. Olstein; Alan J. Grant

(57) ABSTRACT

Therapeutically effective anti-viral compositions, useful especially against respiratory diseases caused or mediated by respiratory syncytial virus (RSV) are disclosed, wherein said compositions comprise at least one anti-RSV antibody, including high affinity antibodies, and an additional anti-inflammatory agent, especially corticosteroids, as well as anti-inflammatory antibodies, especially anti-interleukin-6. Also disclosed are methods of using such compositions to treat and/or prevent respiratory diseases. Such compositions may optionally contain other non-antibody anti-viral agents.

10 Claims, 21 Drawing Sheets

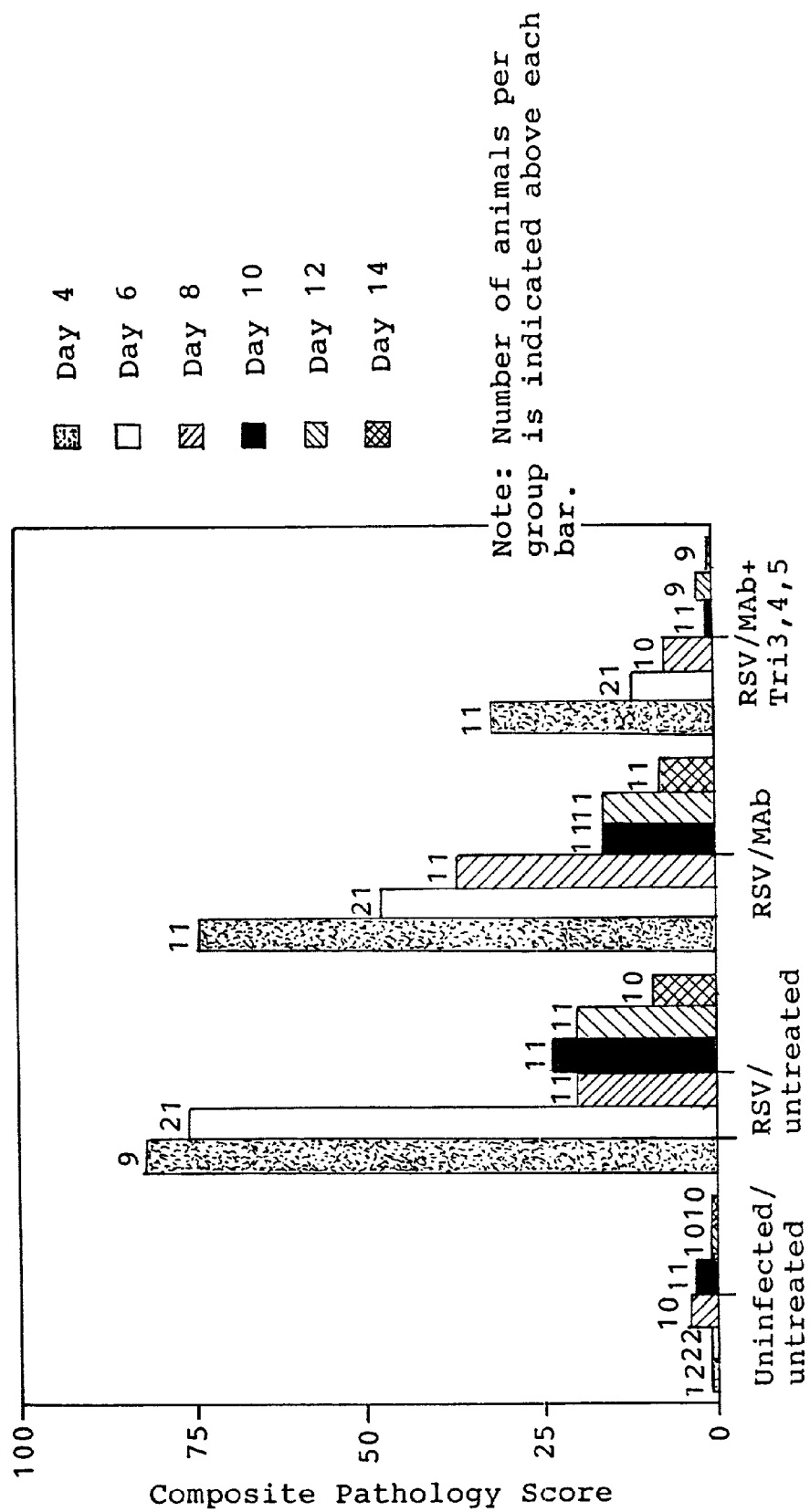

FIG. 2A

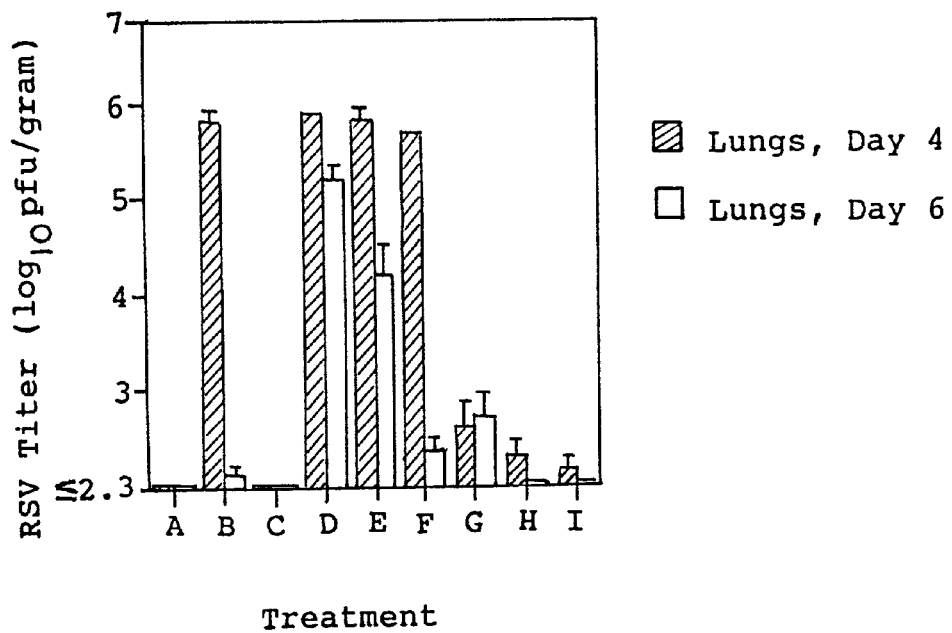

Combined Synagis-triamcinolone Therapy of RSV Pneumonia Cotton Rats

- A: uninfected/untreated
- B: RSV/untreated
- C: RSV/Synagis (15 mg/kg x1). i.m.
- D: RSV/Triamcinolone (16 mg/kg x 3). i.m.
- E: RSV/Triamcinolone (4 mg/kg x3). i.m.
- F: RSV/Triamcinolone (1 mg/kg x3). i.m.
- G: RSV/Synagis (15 mg/kg X 1).i.m. + Triamcinolone (16 mg/kg x3). i.m.
- H: RSV/Synagis(15 mg/kg x1). i.m. + Triamcinolone (4mg/kg x 3). i.m.
- I: RSV/Synagis (15 mg/kg x1). i.m. + Triamcinolone (1 mg/kg x3). i.m. +

NOTE: THERE WERE 9-12 ANIMALS FOR EACH TIME POINT

Synagis/Triamcinolone therapy of RSV

Treatment

1: uninfected/untreated
2: RSV/untreated
3: RSV/Synagis (15mg/kg)i.m.
4: RSV/Triamcinolone (16mg/kg)i.m.
5: RSV/Triamcinolone (4mg/kg)i.m.
6: RSV/Triamcinolone (1mg/kg)i.m.
7: RSV/Synagis (15mg/kg)i.m.+Triamcinolone (16mg/kg)i.m.
8: RSV/Synagis(15mg/kg)i.m.+Triamcinolone (4mg/kg)i.m.
9: RSV/Synagis(15mg/kg)i.m.+Triamcinolone (1mg/kg)i.m.

1: uninfected/untreated
2: RSV/untreated
3: RSV/Synagis (15mg/kg)i.m.
4: RSV/Triamcinolone (16mg/kg)i.m.
5: RSV/Triamcinolone (4mg/kg)i.m.
6: RSV/Triamcinolone (1mg/kg)i.m.
7: RSV/Synagis (15mg/kg)i.m.+Triamcinolone (16mg/kg)i.m.
8: RSV/Synagis(15mg/kg)i.m.+Triamcinolone (4mg/kg)i.m.
9: RSV/Synagis(15mg/kg)i.m.+Triamcinolone (1mg/kg)i.m.

Synagis/Triamcinolone Therapy of RSV Alveolitis

Treatment

1: uninfected/untreated
2: RSV/untreated
3: RSV/Synagis (15mg/kg)i.m.
4: RSV/Triamcinolone (16mg/kg)i.m.
5: RSV/Triamcinolone (4mg/kg)i.m.
6: RSV/Triamcinolone (1mg/kg)i.m.
7: RSV/Synagis (15mg/kg)i.m.+Triamcinolone (16mg/kg)i.m.
8: RSV/Synagis(15mg/kg)i.m.+Triamcinolone (4mg/kg)i.m.
9: RSV/Synagis(15mg/kg)i.m.+Triamcinolone (1mg/kg)i.m.

Treatment

1: uninfected/untreated
2: RSV/untreated
3: RSV/Synagis (15mg/kg)i.m.
4: RSV/Triamcinolone (16mg/kg)i.m.
5: RSV/Triamcinolone (4mg/kg)i.m.
6: RSV/Triamcinolone (1mg/kg)i.m.
7: RSV/Synagis (15mg/kg)i.m.+Triamcinolone (16mg/kg)i.m.
8: RSV/Synagis(15mg/kg)i.m.+Triamcinolone (4mg/kg)i.m.
9: RSV/Synagis(15mg/kg)i.m.+Triamcinolone (1mg/kg)i.m.

A: uninfected/untreated
B: RSV/untreated
C: RSV/Synagis (15mg/kg)i.m.
D: RSV/Triamcinolone (16mg/kg)i.m.
E: RSV/Triamcinolone (4mg/kg)i.m.
F: RSV/Triamcinolone (1mg/kg)i.m.
G: RSV/Synagis (15mg/kg)i.m.+Triamcinolone (16mg/kg)i.m.
H: RSV/Synagis(15mg/kg)i.m.+Triamcinolone (4mg/kg)i.m.
I: RSV/Synagis(15mg/kg)i.m.+Triamcinolone (1mg/kg)i.m.

Synagis/Triamcinolone Therapy of RSV

Treatment

1: uninfected/untreated
2: RSV/untreated
3: RSV/Synagis (15mg/kg)i.m.
4: RSV/Triamcinolone (16mg/kg)i.m.
5: RSV/Triamcinolone (4mg/kg)i.m.
6: RSV/Triamcinolone (1mg/kg)i.m.
7: RSV/Synagis (15mg/kg)i.m.+Triamcinolone (16mg/kg)i.m.
8: RSV/Synagis(15mg/kg)i.m.+Triamcinolone (4mg/kg)i.m.
9: RSV/Synagis(15mg/kg)i.m.+Triamcinolone (1mg/kg)i.m.

Combined Synagis-Triamcinolone Therapy of RSV in Cotton Rats:

Combined Synagis-Triamcinolone Therapy of RSV in Cotton Rats: Rebound of Histopathology Group D: RSV/Synagis-Triam, short-term
Group E: RSV/Synagis-Triam, long-term, high dose
Group F: RSV/Synagis-Triam, long-term, high/low

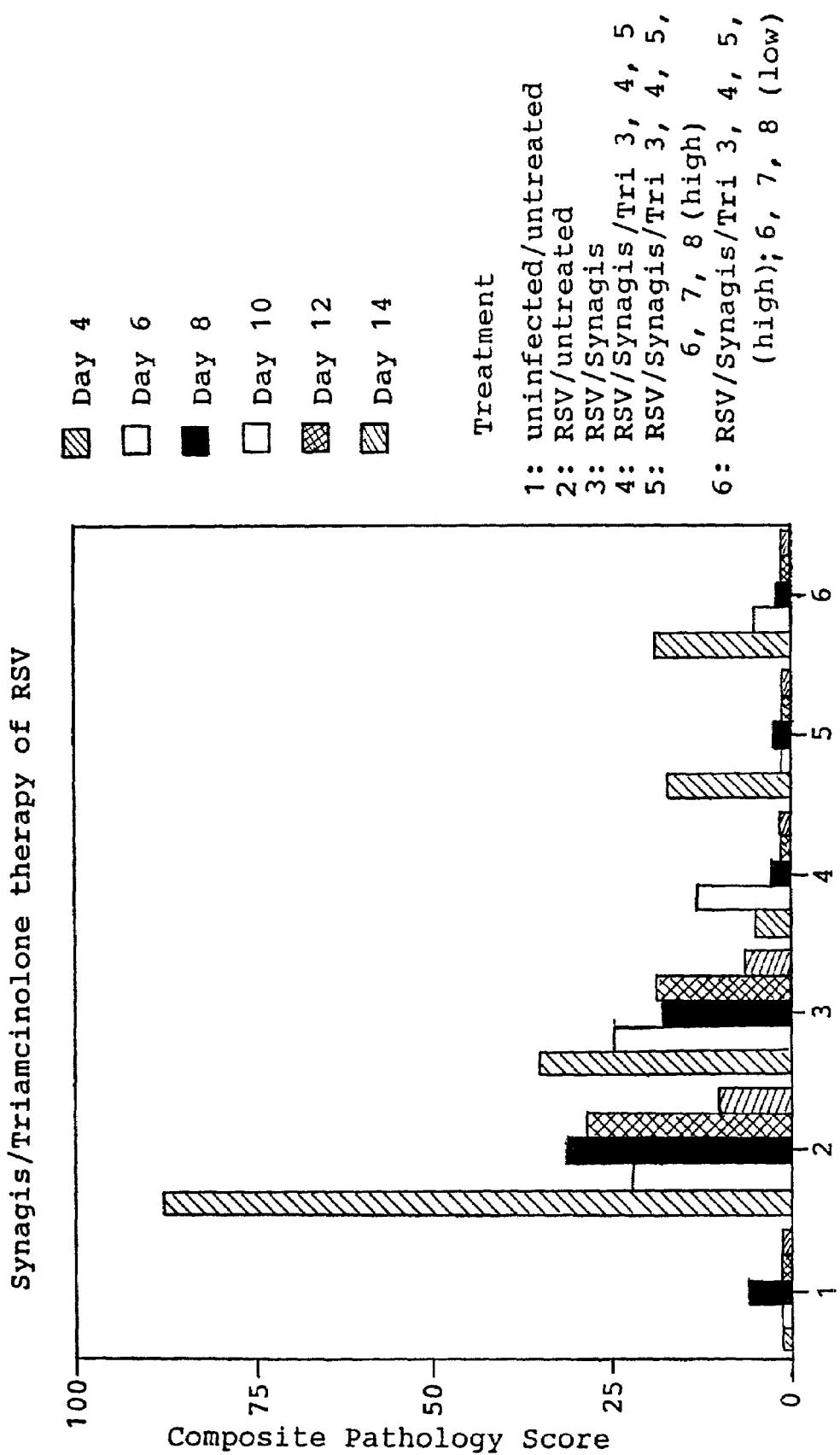

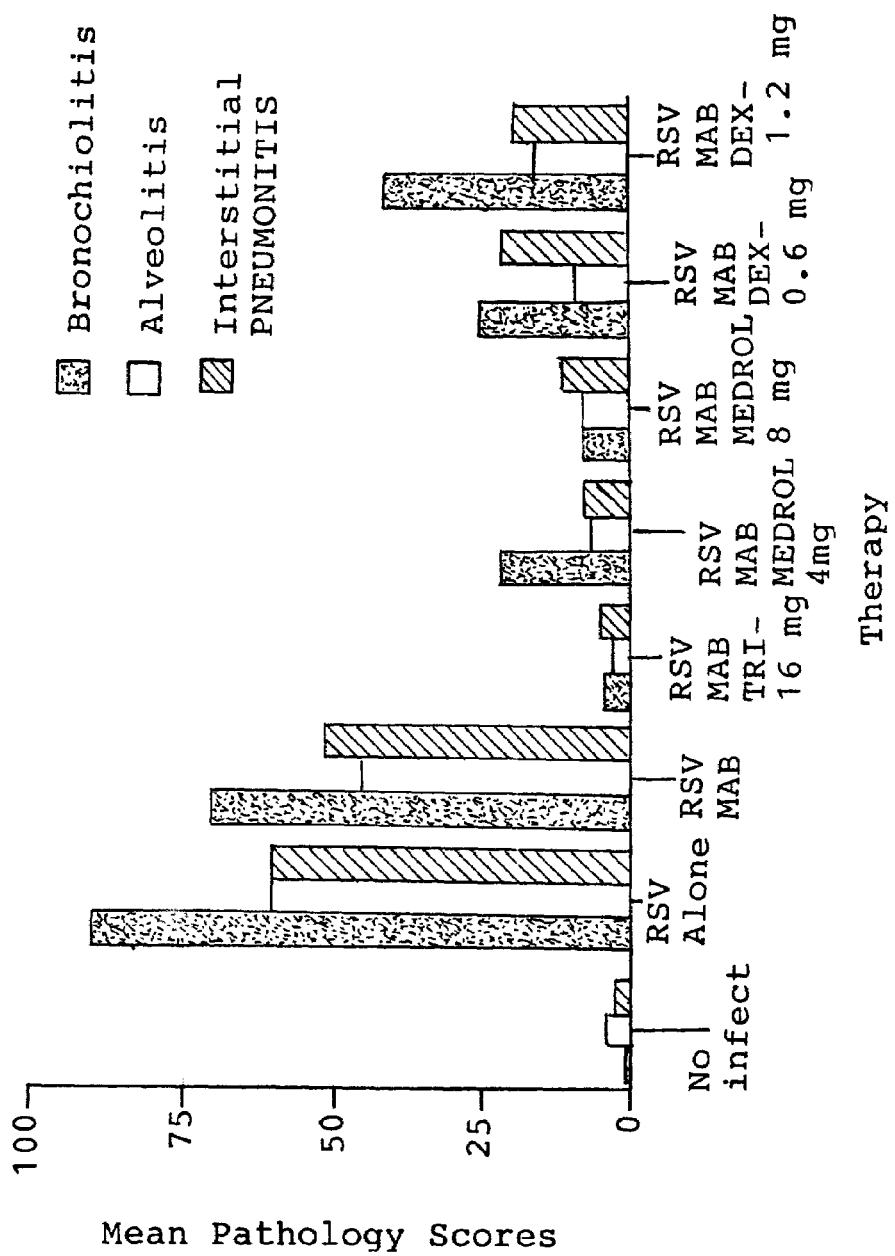

Combined Synagis-steroid Therapy of RSV Pneumonia in Cotton Rats

Groups

Group 1 - unifected/untreated
Group 2 - RSV i.n./untreated
Group 3 - RSV i.n./Synagis i.m.
(15mg/kg)+Triamcinolone i.m.(16mg/kg)

RPA's of RSV-Infected Cotton Rat Lungs

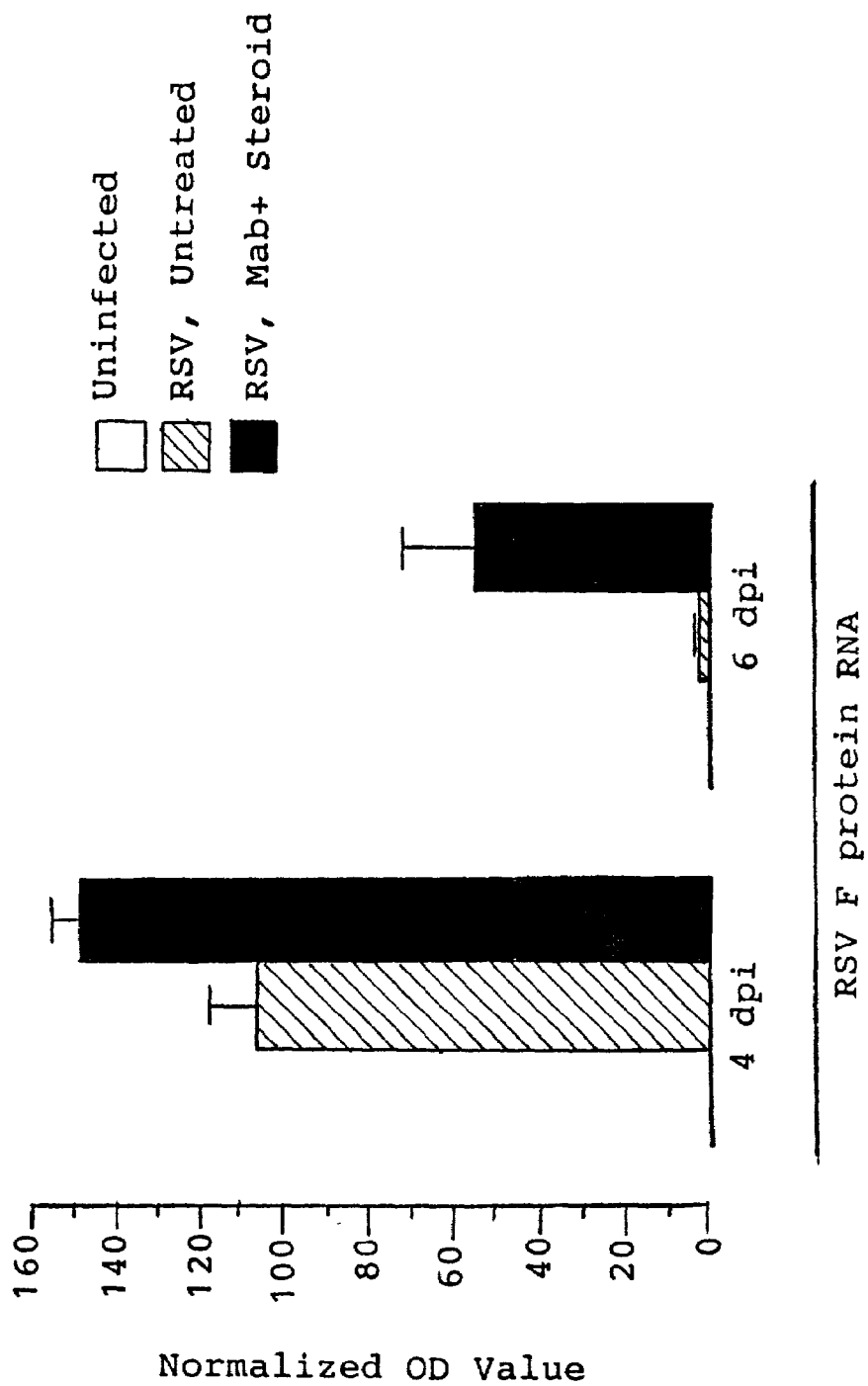

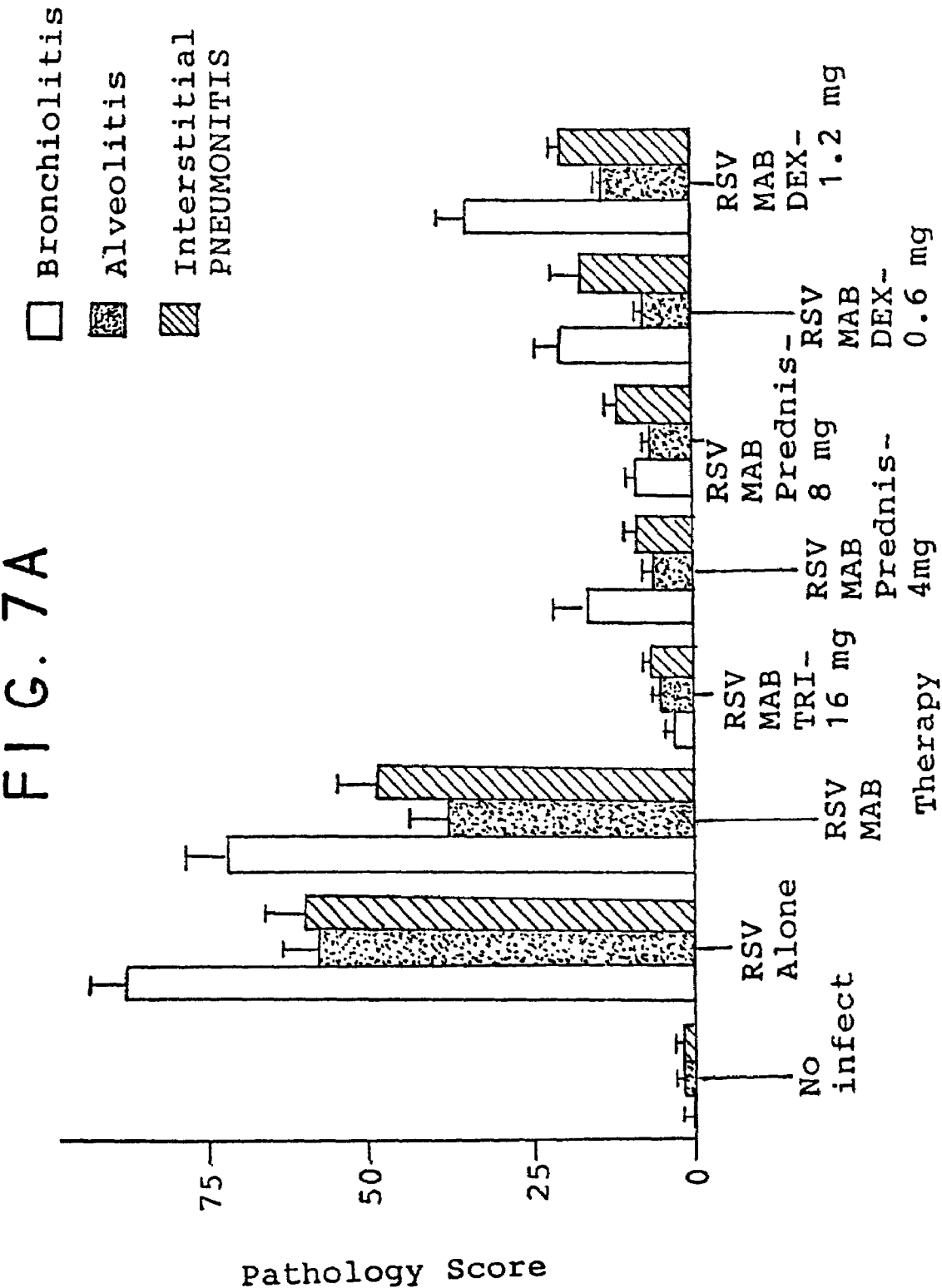

United States Patent US 7,208,162 B2

COMBINATION THERAPY OF RESPIRATORY DISEASES USING ANTIBODIES AND ANTI-INFLAMMATORY AGENTS

This application claims the benefit of priority of U.S. Provisional Application 60/201,404, filed May 3, 2000, the disclosure of which is hereby incorporated by reference in its entirety.

FIELD OF THE INVENTION

The present invention relates to novel compositions comprising antibodies and anti-inflammatory agents, including steroids, with optional addition of antiviral agents useful in the treatment and/or prevention of disease and the symptoms incident to disease, especially respiratory diseases.

BACKGROUND OF THE INVENTION

The current incidence of infection caused by resistant or difficult to control microbes, including both viruses and bacteria, has created a need for newer approaches to controlling such organisms, as well as to treating those already infected.

Among the more difficult infectious agents to control and treat are the viruses. For example, respiratory syncytial virus (RSV) is a major cause of acute respiratory illness in young children admitted to hospitals and the major cause of lower respiratory tract infection in young children. A major obstacle to producing an effective vaccine against such agents as RSV has been the issue of safety. Conversely, the use of immunoglobulins against such viral agents has proven of some value. For example, studies have shown that high-titred RSV immunoglobulin was effective in prophylaxis for RSV infections in animal models. However, immunoglobulins, while highly effective in animals when used prophylactically, were minimally effective when used therapeutically. Thus, the use of antibodies to treat animals, such as humans, without some additional source of therapy may prove relatively ineffective. Consequently, use of antibodies with additional agents might be more useful and the identification of such agents for combination therapy with antibodies is a teaching of the present invention. The present invention solves problems experienced by previous treatment regimens by combining different forms of therapy as a means of treating the disease. For example, treatment with neutralizing antibody alone fails to address concerns over inflammation whereas treatment with anti-inflammatory agents alone fails to check the progress of the virus. Thus, treatment of RSV with steroids, shown in some cases to have little effect when administered systemically rather than topically, is shown herein to have a greater effect when administered systemically along with a potent neutralizing antibody.

Bacteria also present a formidable challenge in the area of disease control and prevention. This is especially true with the rise of nosocomial infections in hospitals and elsewhere and the use of high-titred antibodies in controlling such infections would be a welcomed solution to this problem.

As a result, an alternative approach to microbial therapy has been the development of antibodies, especially neutralizing monoclonal antibodies, with high specific neutralizing activity. One drawback to this route has been the need to produce human antibodies rather than those of mouse or rat and thus minimize the development of human anti-mouse or anti-rat antibody responses, which potentially results in immunopathology.

One alternative approach has been the production of antibodies in which the genes encoding the mouse heavy and light chain variable regions have been coupled to the genes for human heavy and light chain constant regions to produce chimeric, or hybrid, antibodies.

In some cases, mouse CDRs have been grafted onto human constant and framework regions with some of the mouse framework amino acids being substituted for correspondingly positioned human amino acids to provide a "humanized" antibody. [U.S. Pat. Nos. 5,693,761 and 5,693,762].

A humanized anti-RSV antibody with good affinity has been prepared and is currently being marketed.

In addition, a number of other therapeutic agents useful against such viruses as respiratory syncytial virus (RSV), as well as parainfluenza virus (PIV), have made their appearance. However, some of these chemical agents, such as ribavirin, have presented drawbacks. Thus, for example, ribavirin, although currently licensed for therapy of RSV pneumonia and bronchiolitis (Hall et al, *N. Engl. J. Med.*, 308: 1443 (1983); Hall et al., *JAMA*, 254:3047 (1985), is still of controversial value [see: Ohmit et al, *J. Clin. Epidemiol.*, 49, 963 (1996)] and has to be administered over an 18 hour period daily by aerosol inhalation. In addition, the level of secondary infection following cessation of treatment is significantly higher than in untreated patients.

While the beneficial effects of such known antibodies as palivizumab and RespiGam® (both produced by Medimmune, Gaithersburg, Md.) has been demonstrated, there has yet to be shown a role for such agents as corticosteroids in the therapy of respiratory syncytial virus (RSV) bronchiolitis and pneumonia. While some of the problems may have been due to inconsistencies in the choice and dosage of the steroids utilized, the combination of corticosteroids with antibodies such as those mentioned herein has been shown to greatly reduce viral titers without altering the degree of inflammation. (see Prince et al, J. Inf. Dis., (2000), infra) Thus, the present invention has solved much of the problem by achieving dramatic reduction in lower respiratory infection (LRI) in animals using steroids in combination with a monoclonal antibody against RSV.

BRIEF SUMMARY OF THE INVENTION

The present invention is directed to compositions comprising a neutralizing monoclonal antibody, including high affinity antibodies, against respiratory viruses, as well as other organisms causing respiratory disease and/or distress, as well as other therapeutic agents useful in the treatment of respiratory disease.

In accordance with an aspect of the present invention, there is provided therapeutic compositions containing a neutralizing antibody, including high affinity antibodies, as well as one or more additional anti-inflammatory agents capable of working in concert to treat and/or prevent antiviral infections, especially those of the respiratory system, most especially diseases caused by RSV.

In one embodiment, the therapeutic composition of the present invention comprises an anti-RSV antibody, including high affinity antibodies, useful in treating and/or preventing virally induced respiratory disease, and an additional anti-inflammatory agent useful in managing RSV infection.

In a separate embodiment, the present invention is also directed to compositions comprising an anti-RSV neutralizing antibody, including high affinity antibodies, and an additional anti-inflammatory agent, the latter being effective against inflammations accompanying RSV infection, such as infections by other viruses, for example, parainfluenza virus (PIV), as well as by bacteria, fungi, and various other parasites.

In a preferred embodiment, the neutralizing monoclonal antibody used in the compositions of the present invention is an antibody disclosed in U.S. Pat. No. 5,824,307 (the disclosure of which is hereby incorporated by reference in its entirety). The use of structural variants of this antibody is also specifically contemplated by the present invention.

In one preferred embodiment, a therapeutic composition of the present invention comprises an anti-RSV neutralizing antibody, including high affinity antibodies, most preferably an antibody specific for the F epitope of RSV, or a variant thereof, including active fragments thereof, and an anti-inflammatory agent, especially an anti-inflammatory agent, including steroids, having therapeutic value in the treatment of viral diseases of the respiratory system, preferably diseases caused by RSV, influenza and PIV.

In a most preferred embodiment of the present invention, the anti-inflammatory agent is itself an antibody.

In another most preferred embodiment of the present invention, the therapeutic composition comprises an anti-RSV neutralizing antibody, including high affinity antibodies, an anti-Interleukin-6 (anti-IL-6) antibody and a non-antibody anti-inflammatory agent, such as a anti-inflammatory agent, including a steroid.

In a preferred embodiment, said anti-inflammatory agent is a steroid, especially a corticosteroid. In a most preferred embodiment, the antibody is an antibody specific for the F antigen of RSV, especially an antibody with the same epitope specificity of an antibody as disclosed in U.S. Pat. No. 5,824,307, or an immunologically active variant thereof, and the anti-inflammatory agent, including a steroid, is selected from the group consisting of cortisone, hydrocortisone, prednisone, prednisolone, methylprednisolone, triamcinolone, betamethasone, beclamethasone and dexamethasone.

Other anti-inflammatory agents useful in the compositions of the present invention include, but are in no way limited to, ibuprofen, indomethacin, acetylsalicylic acid, and acetaminophen.

An additional object of the present invention is to provide anti-microbial compositions comprising anti-microbial antibodies, anti-inflammatory agents, and, optionally, an additional anti-microbial agent, such as an anti-viral agent, for example, ribavirin, amantadine, rimantadine, or a neuraminidase-inhibitor.

BRIEF DESCRIPTION OF THE DRAWINGS

FIG. 1 shows the results of RSV therapy employing a composition of the present invention. Here, the therapeutic composition employs an anti-RSV antibody (called commercially palivizumab) and triamcinolone. Here, the anti-RSV antibody is an IgG immunoglobulin that is useful in treating respiratory diseases caused by viruses (See: *Pediatrics*, 102 (3 Pt. 1), pp. 531–537 (1998)), such as RSV and PIV and whose sequence is described as Medi-493 in Johnson et al, *J. of Infectious Diseases*, 176, 1215–1224 (1997) or in FIGS. 7 and 8 of U.S. Pat. No. 5,824,307, the disclosures of both of which are hereby incorporated by reference in their entirety. The results represent a combination of the results of Example 1 (repeated in its entirety to give two complete sets of data) and part of the results of Example 2.

FIG. 5 shows the results of antibody/steroid combination therapy on RSV pneumonia in cotton rats using several different steroids with the same antibody. Treatment doses for each group of animals is shown at the bottom of the histogram.

FIG. 1A shows arithmetic mean pulmonary scores (plus standard error) for the degree of bronchiolitis, alveolitis, and interstitial pneumotitis seen in cotton rats on day 6 following infection with $10^{6.5}$ pfu of respiratory syncytial virus (excluding the uninfected controls) following the indicated therapy. Each group represents 8 or 9 animals. FIG. 1B shows the composite pathology scores after infection with $10^{6.5}$ pfu of respiratory syncytial virus, with sampling of pulmonary histopathology on days 6, 8, 10, 12, and 14 after the indicated therapy. Each group represents 3 or 4 animals.

DETAILED SUMMARY OF THE INVENTION

Figure 2B:
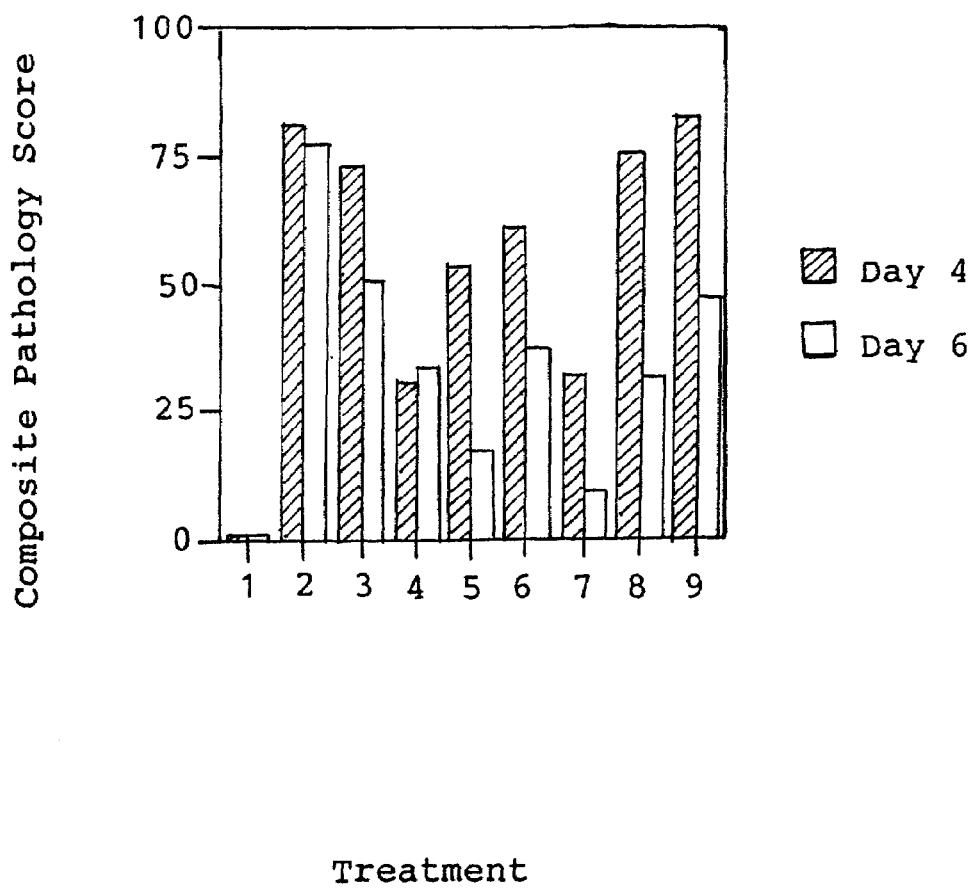
FIG. 2 shows the results of treatment of cotton rats infected with respiratory syncytial virus using combined antibody/steroid therapy. Panel A shows RSV titer for each of the groups of animals whose treatment is described in Example 1. Panel B shows the results for composite pathology score, panel C the peribronchiolitis score, panel D the alveolitis score, and panel E the interstitial pneumonitis score.
Figure 2C:
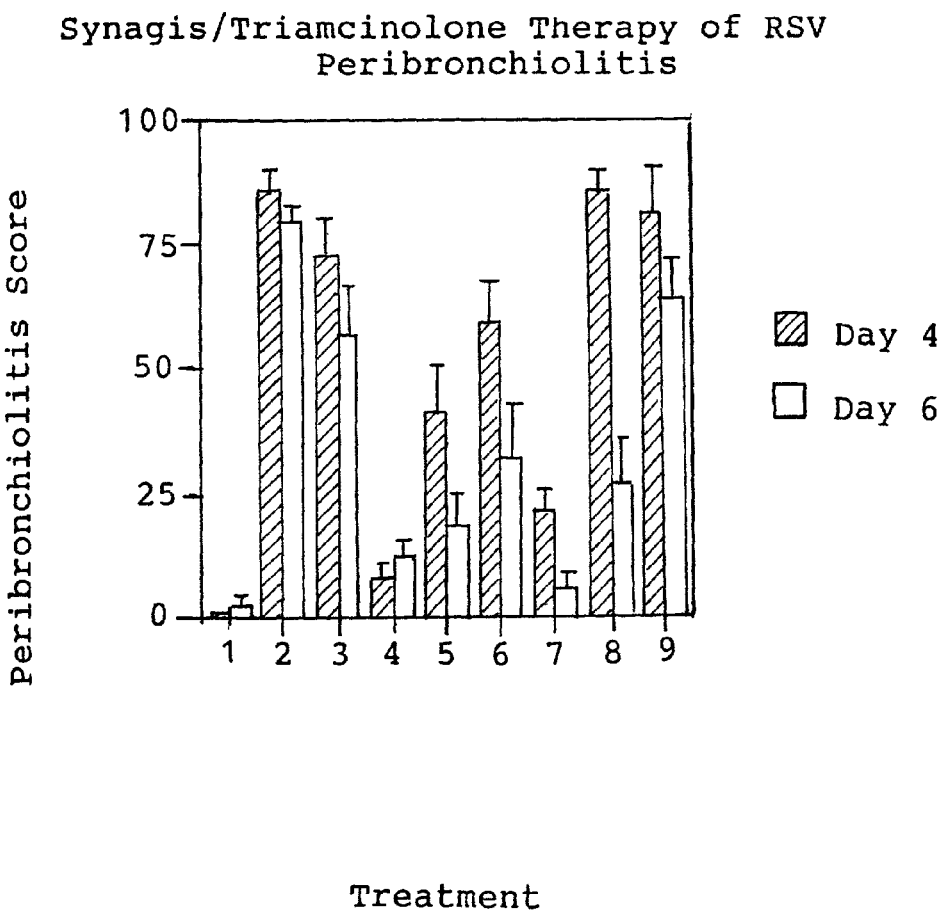
Figure 2D:
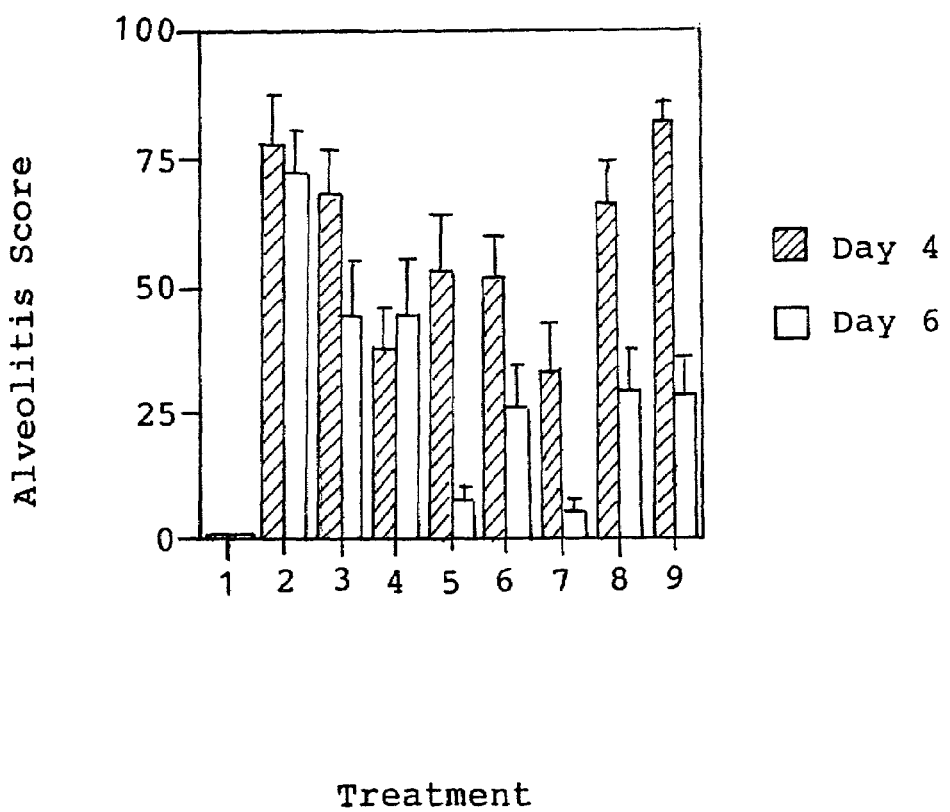
Figure 2E:
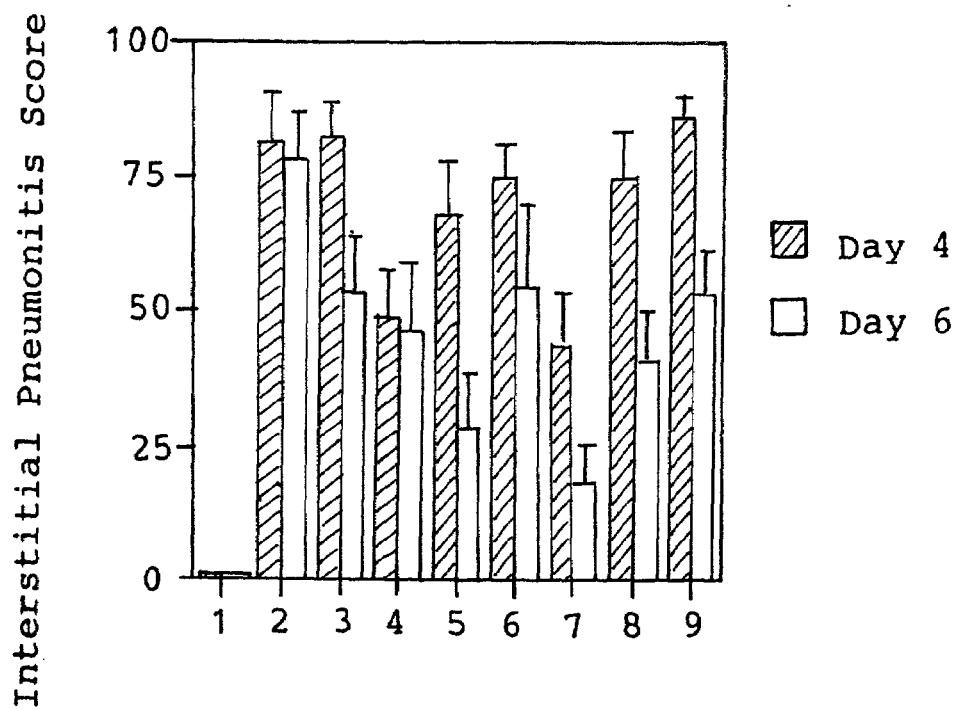

One problem facing clinicians in their attempts to control virus-induced infections is the inflammation of sensitive and delicate respiratory tissues that often accompanies such infection as the respiratory system attempts to respond to the infection.

One solution to this problem is presented by the compositions of the present invention, which is directed to therapeutically effective compositions comprising a neutralizing monoclonal antibody, including high affinity antibodies, against respiratory viruses, such as, for example, respiratory syncytial virus (RSV), and even parainfluenza virus (PIV), influenza A, influenza B, influenza C, and the like, as well as related viral agents causing respiratory disease, and other therapeutic agents, including other antibodies and non-antibody agents, useful in the treatment of respiratory disease and the amelioration of inflammation caused by such infections.

The compositions and treatments according to the present invention represent a solution to this problem by taking advantage of the unique abilities of antibodies, especially those utilized herein, to control the ravages of bacterial and viral infections, most especially as they affect the delicate tissues of the respiratory system, and thereby offset the otherwise deleterious effects of relying solely on highly potent, and potentially toxic, anti-microbial agents that must, because of their chemical and biological properties, perforce be administered in sparing, and sometimes less than effective, dosages.

It is thus an object of the present invention to provide therapeutic compositions comprising an antibody, such as a neutralizing antibody, including a high affinity neutralizing antibody, especially an anti-RSV antibody, most especially an antibody having the same affinity as an antibody whose variable chain sequences are disclosed in FIGS. 7 and 8 of U.S. Pat. No. 5,824,307, such as antibodies with an affinity and specificity similar to the aforementioned palivizumab (used in the experiment of FIG. 1), including all immunologically active variants and fragments thereof, as well as one or more additional agents capable of working either separately or in concert to treat and/or prevent inflammation of the respiratory system caused by infection with viral agents, such as RSV and PIV. Such compositions also serve to combat and/or relieve the deleterious physiological and/or immunological effects of such infections, especially infections of the respiratory system, most especially diseases caused by RSV, or PIV, and/or other viruses.

Thus, the present invention relates to a composition comprising a therapeutically effective amount of an antibody, such as a neutralizing antibody, including a high affinity neutralizing antibody, and including active variants and fragments thereof, having specificity for one or more epitopes of respiratory syncytial virus (RSV), and at least one anti-inflammatory agent capable of relieving the effects of inflammation caused by viral infection and wherein such agents are suspended in a pharmacologically acceptable carrier, including all acceptable diluents and/or excipients.

Antibodies, such as Palivizumab, useful in the present invention can include a whole antibody molecule (i.e., a tetrameric structure with the common $H_2L_2$ arrangement) or active fragments thereof. Such fragments include, but are not limited to, Fab, $F(ab')_2$, single chain antibodies, chimeric antibodies, such as human-murine chimeric antibodies, humanized antibodies, the latter being formed from human framework and constant regions with complementarity determining regions (CDRs) derived from a species other than human, such as murine, as well as completely synthetic (i.e., recombinant) antibodies having amino acid sequences different from those of any antibody produced in nature or thus far created by man. Such wholly synthetic antibodies may be produced by cloning in recombinant cells produced for such purposes or by direct chemical synthesis in vitro.

The anti-viral, e.g. anti-RSV, neutralizing antibody of the present invention can also include antibody molecules, and active fragments thereof, having a different amino acid sequence from an antibody as disclosed in U.S. Pat. No. 5,824,307 (and thus be a variant thereof) so long as good potency against the respiratory virus, such as RSV or other disease-causing microbial agent, is maintained.

In accordance with the present invention, the antibodies useful in the methods disclosed herein typically have affinity constants for their respective antigenic epitopes that are in the range of no greater than about 1 nM (or at least about $10^{-9}$ M). Because such high affinities are not easily measured, except by the procedures described herein, such value may commonly be considered as part of a range and may, for example, be within 100 fold of the nM values recited herein. Thus, they may be about 100 fold greater ($10^{-7}$ M) or lower ($10^{-11}$ M) than this value, or may equal this value, and still be useful in the present invention. Because this is a dissociation constant, the higher the value, the greater the degree of dissociation of the antigen and antibody and thus the lower the affinity. Such values may be easily converted to association constants by taking the reciprocal of the dissociation constant and adjusting the units to reciprocal molar in place of molar. In such case, the affinity of the antibody for its antigen will increase with increasing association constants. Such neutralizing antibodies are known in the art (see, for example, antibodies disclosed in FIGS. 7 and 8 of U.S. Pat. No. 5,824,307 where the affinity is denoted by a dissociation constant, which is in the nature of a binding constant, so as to give units of molarity). As used herein, high affinity would constitute a dissociation constant of about $10^{-9}$ M or lower. As such, the affinity of the antibody for antigen is inversely proportional to the value of this constant (i.e., the higher the constant, the lower the affinity). Such a constant is readily calculated from the rate constants for the association-dissociation reactions as measured by standard kinetic methodology for antibody reactions (see U.S. Pat. No. 5,824,307 for a suggested method of doing this).

The compositions of the present invention are not limited in their mode of administration to the patient. Thus, such administration can include parenteral as well as oral administration, and thus include intravenous, intramuscular, pulmonary and any type of systemic administration. In administering the combination therapy of the present invention, it should be clearly borne in mind that the effects realized by such treatment are the result of the combination of agents utilized herein but that such agents need not necessarily be administered simultaneously or as part of the same mixture and may, if suitable, be administered at different times and in independent dosages calculated to have the maximal overall therapeutic effect although these effects may be separately realized by the different components of the claimed compositions.

In other embodiments, the composition of the present invention comprises an anti-RSV antibody, including high affinity antibodies, in addition to an antibody whose specificity is directed toward some other viral agent. Such embodiments include compositions comprising additional anti-RSV antibodies, including high affinity antibodies. A specific embodiment of such a composition comprises an antibody as disclosed in FIGS. 7 and 8 of U.S. Pat. No. 5,824,307 and an additional anti-RSV antibody.

The compositions of the present invention may also comprise a non-antibody antiviral agent, or other antimicrobial agent, in addition to the neutralizing antibody(ies) and anti-inflammatory agents ordinarily comprising the compositions disclosed herein. Such compositions may include a single antiviral agent or two or more antiviral agents, either at similar or different concentrations and dosages, depending on the effectiveness of the agent against the virus in question as well as on the needs of the patient and the determinations and inclination of the clinician, in whose sound discretion such decisions are left. In a preferred embodiment, said antiviral agent is a potent anti-viral chemical agent, but may also be some other anti-viral antibody. Thus, a preferred composition according to the present invention includes a mixture of anti-viral antibodies, or a mixture of anti-viral and anti-bacterial antibodies, with differing specificities, and an anti-inflammatory agent, including steroids and anti-inflammatory antibodies.

Evidence for the efficacy of utilizing treatment of such respiratory diseases as bronchiolitis and pneumonia using antibody and glucocorticoid in combination is known. (See: Prince et al, *J. Infectious Diseases*, 182: 1326–30 (2000), combining the monoclonal antibody palivizumab with triamcinolone acetonide in cotton rats (*Sigmodon hispidus*), the disclosure of which is hereby incorporated by reference in its entirety).

An anti-viral agent such as ribavirin can be given orally whereupon its bioavailability is about 45% with peak concentrations in plasma after about 1 to 2 hours. Single adult doses are in the 600 to 1200 mg range. The general route of administration for ribavirin is by aerosol with a dose to infants of about 1.4 mg/kg of body weight per hour and treatment for about 12 to 18 hours per day over a 3 to 7 day period. However, the dosage for the particular anti-viral agents (such amantadine, rimantadine, or a neuraminidase-inhibitor) that may be administered along with the antibodies and anti-inflammatory agents of the present invention may be different depending on the agent and the severity of the condition to be treated. Despite such considerations, the dosages of such non-antibody agents for use in the combination therapies disclosed herein will commonly differ only slightly, if at all, from the dosages normally used in treating the disease in question.

In accordance with the present invention, the pathology due to RSV is due to both direct tissue destruction and inflammation due to recruitment of immune cells, cytokines and chemokines. Combination therapy for RSV, such as that involving antiviral and anti-inflammatory agents, is known in the art. [se: Prince et al., U.S. Pat. No. 5,290,540]. Indeed, some corticosteroids have been found not particularly useful for treating inflammation due to RSV. Those cases involved systemically administered corticosteroids (see, for example, the reported ineffectiveness of systemically administered prednisolone in infant RSV, in Bulow et al, Prednisolone treatment of Respiratory Syncytial Virus Infection: a randomized controlled trial of 147 infants, *Pediatrics,* 104 (Dec. 6, 1999), p e77). Conversely, the use of such agents in conjunction with an authentic anti-viral (i.e., anti-RSV) antibody, such as a neutralizing antibody, including high affinity antibodies, such as those disclosed herein for use in the therapies of the present invention, especially where the proper dose and steroid are selected for such use, provides a novel and effective approach to treating respiratory infections by combination therapy (see the results provided by FIG. 1).

As described in the literature, it may not be of much value to eliminate the effects of viral infection of cells of the respiratory system using antiviral agents and antibodies directed against such viruses if, in fact, the viral condition has already triggered an inflammatory effect (i.e, an immunological effect) that will continue to aggravate the disease condition long after the viral agent itself has been eliminated from the infected area. [see: Prince and Porter, *J. Infect. Dis.,* 173:598 (1996)]. To avoid such undesirable after effects of treatment with an antiviral agent, such as the antibodies and other anti-viral agents useful in the present invention, it is desirable to have an effective anti-inflammatory regimen in place.

In view of the foregoing, the present invention also relates to a composition comprising a therapeutically effective amount of an anti-microbial neutralizing antibody, including high affinity antibodies, and including immunologically active variants and fragments thereof, having specificity for one or more epitopes of respiratory syncytial virus (RSV) and at least one anti-inflammatory agent wherein said antibody and agent are suspended in a pharmacologically acceptable carrier, which includes all appropriate diluents and excipients.

In accordance with the disclosure herein, said anti-inflammatory agent can include an antibody or a non-antibody. Where said anti-inflammatory agent is an antibody, a preferred embodiment will include an anti-cytokine or anti-chemokine antibody, for example, an anti-interleukin antibody, especially anti-interleukin-6 (anti-IL-6) antibody, an anti-interferon (anti-IFN) or an anti-tumor necrosis factor (anti-TNF). Such antibodies may be polyclonal or monoclonal in nature.

Also in accordance with the present invention, where said composition comprises an anti-inflammatory agent, said agent may be a anti-inflammatory agent, including a steroid, especially a corticosteroid, said corticosteroid being preferably selected from the group consisting of cortisone, hydrocortisone, prednisone, prednisolone, methylprednisolone, triamcinolone, betamethasone, beclamethasone, and dexamethasone. Such agents may commonly be administered as their corresponding salts but this is not specifically required for practice of the invention herein.

Also in accordance with the present invention, the anti-inflammatory agents may include, but are in no way limited to, such agents as ibuprofen, indomethacin, acetaminophen and acetylsalicylic acid.

An especially preferred embodiment of the compositions of the present invention comprises an anti-RSV antibody, especially palivizumab, and an antiviral agent, for example, and an anti-inflammatory agent, especially a steroid.

Pharmaceutical compositions will comprise sufficient active antibody and antiviral and/or anti-inflammatory agents, so as to produce a therapeutically effective amount of the composition, i.e., an amount sufficient to reduce the amount of infecting virus, for example, RSV. The pharmaceutical compositions will also contain a pharmaceutically acceptable carrier, diluent or excipient, which include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. A thorough discussion of pharmaceutically acceptable excipients is available in REMINGTON'S PHARMACEUTICAL SCIENCES (Mack Pub. Co., N.J. 1991).

The present invention is also directed to methods of treating and/or preventing a respiratory disease, especially diseases caused by respiratory syncytial virus, comprising administering to an animal, especially a human patient, at risk thereof, or afflicted therewith, of a therapeutically effective amount of a composition selected from the group consisting of the compositions disclosed herein.

Thus, the present invention provides a method for treating an animal, especially a human patient, suffering from a lower respiratory disease, such as RSV, and wherein said disease is caused by a microbial agent, especially where said agent has caused, or is likely to cause, an inflammation of the tissues so infected, or tissues surrounding said infected tissues.

Optimum dosages for the anti-RSV antibodies making up the compositions of the present invention may be in the range of 5 to 20 mg/kg of body weight, the optimum for palivizumab being about 15 mg/kg of body weight (when given intravenously). The non-antibody anti-microbial agents, where used in said compositions, other than the antiviral antibodies employed herein, are commonly given in the range of about 1 µg to about 1 gram per kg body weight. The anti-inflammatory agents used in the compositions disclosed herein are commonly in the range of about 1 µg to about 1 gram per kg of body weight. Where said anti-inflammatory agent is a steroid, the range of dosages will be in the range of 10 µg to about 1 gram per kg body weight with a preferred range being about 0.5 mg to about 50 mg per kg of body weight.

An example of a primary infectious agent to be controlled by the compositions and methods of the present invention is respiratory syncytial virus but it is possible that other infectious agents may also be present as opportunistic pathogens. These can include other viruses, especially influenza A, influenza B, and influenza C, and parainfluenza virus (PIV), especially PIV3, some variant or mutant of RSV, a respiratory corona virus and even an adenovirus, and various types of bacterial agents that are either sources of primary infection within the respiratory system or else are agents capable of aggravating existing viral diseases or else weakening the respiratory system so as to make it more susceptible to such viral diseases.

The additional infectious agents acting as opportunistic pathogens are not limited to the viruses and bacteria. Thus, additional infection may be caused by non-viral or bacterial organisms, including various fungi and other parasites. As a result, the compositions according to the present invention may also comprise anti-infectious agents other than antiviral agents. Therapeutically active compositions within the present invention may thus comprise a anti-RSV antibody and an antibacterial agent, including antibiotics, as well as antifungal agents and antiparasitic agents of a broad or narrow spectrum. In addition, all of the latter additional agents may themselves be low or high affinity polyclonal or monoclonal antibodies with specificity against bacteria, or fungi, or other parasites infecting the respiratory system, as well as other related or unrelated systems.

The compositions disclosed according to the present invention for therapy of diseases as recited herein can easily include multiple antibodies against the same or different viruses, or against a virus and an additional microbial infectious agent, or against some non-viral microbial infectious agent, and may additionally include non-immunological agents in combination with said antibodies. In specific embodiments of the present invention, compositions disclosed herein may include an antibody against a virus, such as RSV, plus an antibody against a bacterial agent, especially one that infects the respiratory system, such as that causing tuberculosis, and, optionally, an antiviral agent. A therapeutic composition within the present invention may likewise comprise an anti-viral antibody, a non-immunological anti-viral agent, such as ribavirin, amantadine, rimantadine, or a neuraminidase-inhibitor (these latter three agents being highly useful against influenza), where RSV is the primary infectious agent, and an antimicrobial agent effective in the treatment of some non-viral pathogen, such as bacteria, including the agent of tuberculosis, or against some parasitic agent, and an anti-inflammatory agent, such as any of those already disclosed hereinabove.

Thus, in accordance with the present invention, the anti-infectious agent used in composition with the anti-RSV antibody, including high affinity antibodies, may be an anti-bacterial agent, including but not limited to a macrolide, a penicillin, a cephalosporin, or a tetracycline, or may be an antifungal agent, including but not limited to amphotericin b, fluconazole, or ketoconazole, or an anti-parasitic agent, including but not limited to trimethoprim, pentamidine, or a sulfonamide. The anti-infectious agent may be an anti-viral agent such as ribavirin, amantidine, rimantadine, or a neuraminidase-inhibitor. Such additional agents can also include agents useful against other viruses as well as other agents useful against RSV.

However, in all preferred embodiments of the present invention the primary disease to be treated and/or prevented using the compositions disclosed herein is caused by respiratory syncytial virus (RSV).

With the advent of methods of molecular biology and recombinant technology, it is now possible to produce antibodies for use in the present invention by recombinant means and thereby generate gene sequences that code for specific amino acid sequences found in the polypeptide structure of the antibodies. This has permitted the ready production of antibodies having sequences characteristic of neutralizing antibodies from different species and sources.

In accordance with the foregoing, the antibodies of the present invention are anti-RSV antibodies, most preferably antibodies, whose specificity is toward the same epitope of RSV as the antibody of U.S. Pat. No. 5,824,307, and include all therapeutically active variants and fragments thereof whether produced by recombinant methods or by direct synthesis of the antibody polypeptides.

The anti-RSV antibodies useful in the compositions of the present invention will commonly comprise a mammalian, preferably a human, constant region and a variable region, said variable region comprising heavy and light chain framework regions and heavy and light chain CDRs, wherein the heavy and light chain framework regions are derived from a mammalian antibody, preferably a human antibody, and wherein the CDRs are derived from an antibody of some species other than a human, preferably a mouse. Where the framework amino acids are also derived from a non-human, the latter is preferably a mouse.

In addition, antibodies, including high affinity antibodies, of the invention bind the same epitope as the antibody from which the CDRs are derived, and wherein at least one of the CDRs of said antibody contains amino acid substitutions, and wherein said substitutions comprise the replacement of one or more amino acids in the CDR regions by non-identical amino acids, preferably the amino acids of the correspondingly aligned positions of the CDR regions of the human antibody contributing the framework and constant domains.

The contemplated host intended for treatment or prophylaxis with the compositions disclosed herein is generally an animal, especially a mammal, most especially a human patient.

Another preferred embodiment of the invention provides a method of treating upper and/or lower respiratory tract diseases in a host, especially that caused by respiratory syncytial virus, susceptible to or suffering from such disease, comprising administering to the host a therapeutically effective amount of a composition comprising a anti-RSV antibody, most preferably the antibody disclosed in FIGS. 7 and 8 of disclosed in U.S. Pat. No. 5,824,307, including therapeutically active variants and fragments thereof, an anti-viral agent other than the previously stated anti-RSV antibody, with activity against RSV and an anti-inflammatory agent, said composition being sufficiently active as to produce a therapeutic effect against said disease.

Said composition may be administered by any available means, including but not limited to, oral, intravenous, intramuscular, pulmonary and nasal routes. Such composition may be administered directly to the upper or lower respiratory tract of the host. A typical virus to be treated is respiratory syncytial virus, but other viruses may be treated simultaneously, such as parainfluenza virus, especially type 3. In accordance with the methods of treatment disclosed herein, the anti-viral agent may be human immunoglobulin G, which comprises antibodies against RSV or some other opportunistic virus.

In another preferred embodiment, the invention provides a method of treating respiratory syncytial virus infections of the lower (mostly children) and upper (mostly adults) respiratory tract in a human patient, susceptible to or suffering from such infection, comprising administering to said patient a therapeutically effective amount of a composition of the present invention, said composition comprising a therapeutically effective amount of an anti-RSV antibody and an anti-inflammatory agent, preferably a steroid, most preferably a corticosteroid.

Said therapeutic composition may be administered by any convenient and clinically acceptable route, but will generally be systemically administered and so may be oral, intramuscular, or intravenous, using the composition in the form of a solution or suspension. One of the innovations of the processes of the present invention is the ability to provide effective treatment of diseases, such as RSV pneumonia, and other viral diseases, such as influenza and disease caused by PIV, by systemic treatment.

Such treatment can also include administration of a composition comprising a anti-RSV antibody, as disclosed herein, including therapeutically active variants and fragments thereof, and an additional anti-RSV antibody, including high affinity antibodies, or therapeutically active variants and fragments thereof, and a therapeutically active amount of an anti-inflammatory agent, especially a steroid, most especially a corticosteroid, said composition being effective to produce a therapeutic effect against said disease. Said composition may be in the form of a solution or a suspension. Administration of said composition may be by any desired and effective means, including intravenous and intramuscular. The anti-inflammatory agent may also include a human immunoglobulin G that may be administered systemically. The anti-inflammatory agent may be a corticosteroid.

The compositions of the present invention are useful against a variety of pathological agents, especially those infecting the respiratory system. The compositions according to the present invention may further comprise an additional anti-infectious agent, preferably an antiviral agent, such as ribavirin, but also including other anti-infectious agents effective against viruses other than RSV and including anti-infectious agents effective against opportunistic pathogens, such as viruses other than RSV, including parainfluenza virus, influenza A, influenza B, influenza C, and the like, as well as non-viral pathogens, including bacteria, fungi and various parasites. Of course, other anti-infectious and anti-inflammatory agents known to those skilled in the art are also available for use according to the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned are incorporated herein by reference. Unless mentioned otherwise, the techniques employed or contemplated herein are standard methodologies well known to one of ordinary skill in the art. The materials, methods, and examples are illustrative only and not limiting.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

The following procedure was performed using inbred cotton rats (*Sigmodon hispidus*). On day 0, young adult cotton rats were divided into 9 groups of 12 animals each (total: 108 animals). Identification of each group in terms of treatment was as follows:

| Group | Treatment | |
|---|---|---|
| A | uninfected/untreated | |
| B | RSV/untreated | |
| C | RSV/antibody | (15 mg/kg) |
| D | RSV/triamcinolone | (16 mg/kg) |
| E | RSV/triamcinolone | (4 mg/kg) |
| F | RSV/triamcinolone | (1 mg/kg) |
| G | RSV/antibody triamcinolone | (15 mg/kg)/ (16 mg/kg) |
| H | RSV/antibody triamoinolone | (15 mg/kg)/ (4 mg/kg) |
| I | RSV/antibody triamcinolone | (15 mg/kg)/ (1 mg/kg) |

In each case (Groups B–I), approximately $10^{6.5}$ plaque forming units (pfu) of respiratory syncytial virus (RSV/Long) was administered intranasally in a volume of 100 μl.

On day 3, treatment began as described above for each of the groups. The animals were each weighed and treated according to the indicated regimen. All antibody and steroid administration was intramuscular (i.e., systemic) and both antibody and steroid were administered together. Antibody was palivizumab wherein 15 mg/kg was the dose used in each case. All dosages are given as mg per kg of body weight.

On day 4, six animals from each group were sacrificed, their lungs bisected, with half being homogenized for viral quantitation and the other half being inflated with formalin for histological examination. The remaining six animals in each of groups D through I were treated with the dose of triamcinolone indicated above but no additional antibody was given.

On day 5, the remaining six animals in each group were treated again as described for day 4 (again with no additional antibody).

On day 6, the remaining 6 animals from each group were sacrificed and data collected as described for day 4. Thus, their lungs were bisected, with half being homogenized for viral quantitation and the other half being inflated with formalin for histological examination.

Results of these experiments are shown graphically in FIGS. 2(*a* through *e*). FIG. 2(*a*) shows the results of RSV titer in rats from each group. FIG. 2(*b*) shows a composite pathology score, FIG. 2(*c*) a peribronchiolitis score, FIG. 2(*d*) an alveolitis score, and FIG. 2(*e*) the interstitial pneumonitis score.

In general, the antibody alone accelerated viral clearance when given beginning at 3 days post-infection but had no significant effect on pulmonary pathology. Conversely, administration of the steroids alone had a positive effect on pulmonary pathology but at the cost of retarded viral clearance. The combination of antibody plus steroids showed accelerated viral clearance and accelerated reduction of pulmonary pathology. The experiments performed herein indicated that the optimal doses for the combined regimen were 15 mg/kg antibody (here, palivizumab) and 16 mg/kg triamcinolone.

Figure 3A:
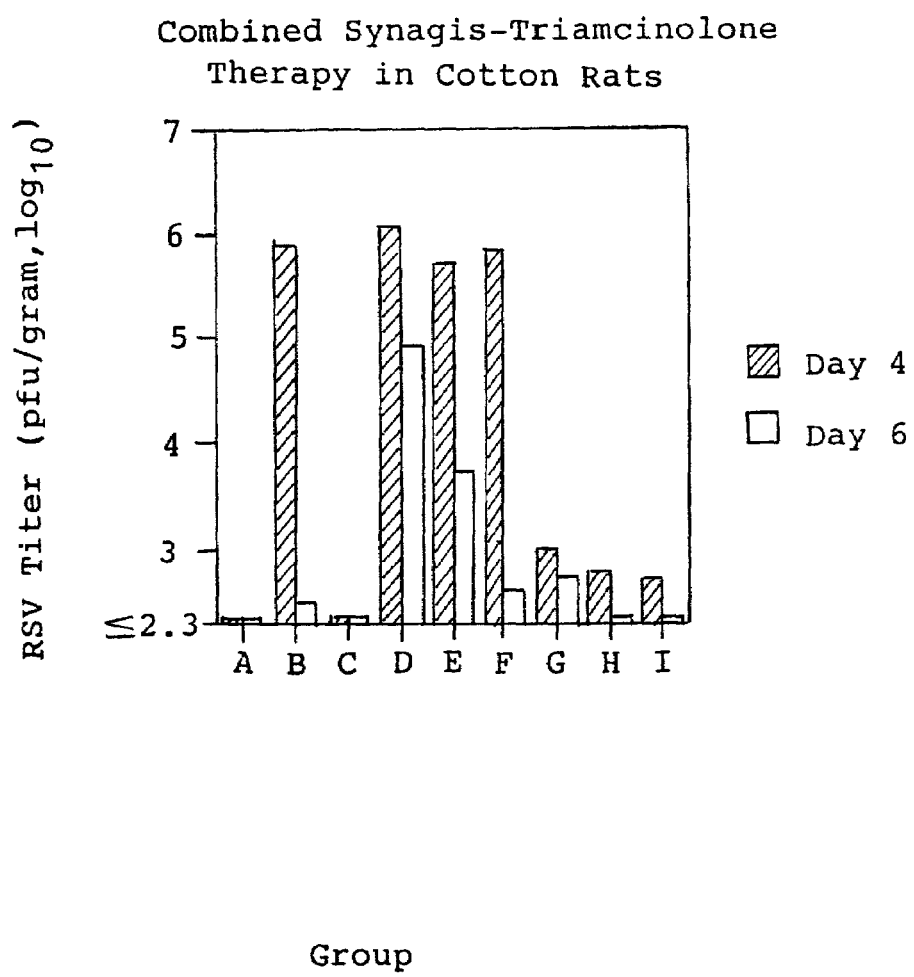
FIG. 3 shows the results of antibody/steroid combination therapy on RSV pneumonia in cotton rats as described in Example 2. Panel A shows the results for virus titer and panel B shows the results for composite pathology score.
Figure 3B:
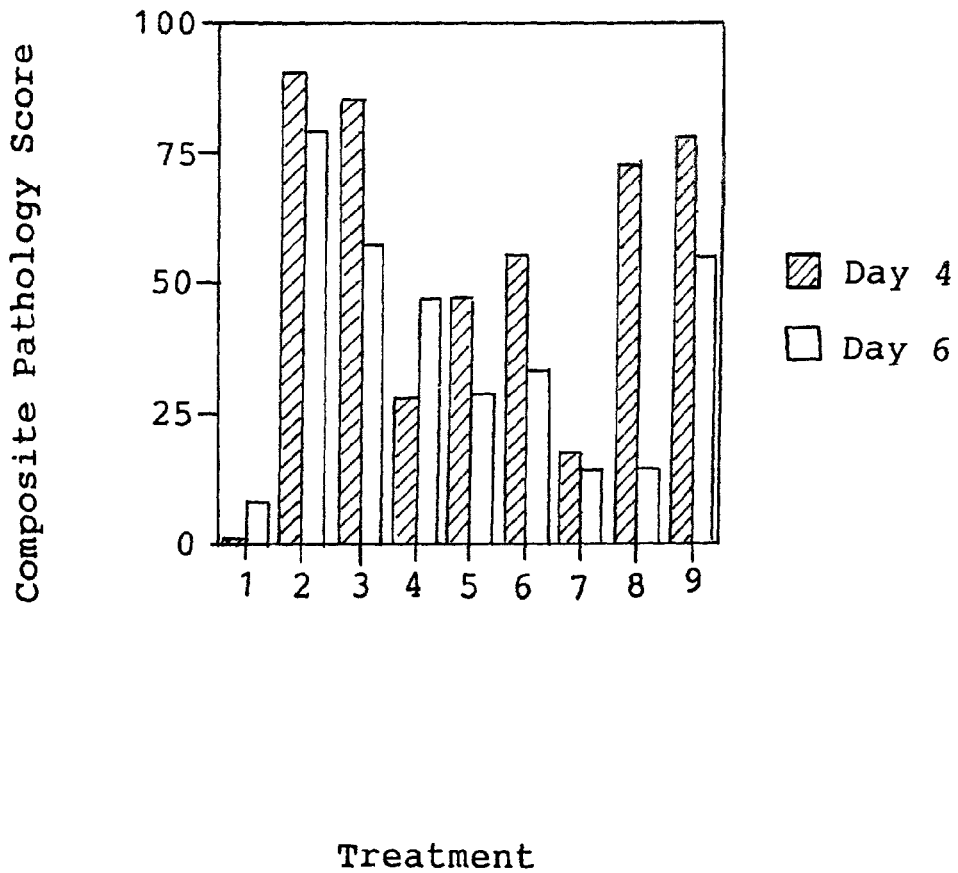

This experiment was duplicated on a separate population of 108 cotton rats divided into groups and treated as just described with similar results reported in FIG. 3 (FIG. 3(a) showing virus titer and FIG. 3(b) showing composite pathology score). The conclusions herein are the result of data from both experiments. The results for composite pathology scores are shown in FIG. 1 reflecting the results of both sets of experiments.

EXAMPLE 2

The following procedure was performed using inbred cotton rats (Sigmodon hispidus). On day 0, 150 young adult cotton rats were divided into 6 groups of 25 animals each. Identification of each group in terms of treatment was as follows:

| Group | Treatment | |
|---|---|---|
| A | uninfected/untreated | |
| B | RSV/untreated | |
| C | RSV/antibody | (15 mg/kg) |
| D | RSV/antibody/triamcinolone | |
| E | RSV/antibody/triamcinolone | |
| F | RSV/antibody/triamcinolone | |

In each case (Groups B–F), approximately $10^{6.5}$ plaque forming units (pfu) of respiratory syncytial virus (RSV/Long) was administered intranasally in a volume of 100 μl.

On day 3, treatment began as described above for each of the indicated groups (here, groups C–F). All animals were treated according to the indicated regimen with the animals in groups C–F receiving antibody and the animals in groups D–F also receiving steroid (triamcinolone). All antibody and steroid administration was intramuscular (i.e., systemic) and both antibody and steroid were administered together. Antibody was palivizumab wherein 15 mg/kg was the dose used in each case. Triamcinolone was administered to each group at a dose of 16 mg/kg. All doses are given as mg per kg of body weight.

On day 4, the animals in each of groups D through F were treated with 16 mg/kg of triamcinolone but no additional antibody was given.

On day 5, the animals were again treated just as on day 4.

On day 6, five animals from each group were sacrificed, their lungs bisected, with half being homogenized for viral quantitation and the other half being inflated with formalin for histological examination. The remaining 6 animals from each group were sacrificed and data collected as described for day 4. Thus, their lungs were bisected, and homogenized, with half being homogenized for viral quantitation and the other half being inflated with formalin for histological examination. The remaining animals were treated as jollows: group E received another dose of triamcinolone at 16 mg/kg while the animals in group F received a 4 mg/kg triamcinolone.

On day 7, the animals of groups E and F were again treated just as on day 6: group E received another dose of triamcinolone at 16 mg/kg while the animals in group F received a 4 mg/kg triamcinolone.

On day 8, five animals from each group were sacrificed, their lungs bisected, with half being homogenized for viral quantitation and the other half being inflated with formalin for histological examination. The remaining animals were treated as follows: group E received another dose of triamcinolone at 16 mg/kg while the animals in group F received a 4 mg/kg triamcinolone.

On day 10, five animals from each group were sacrificed, their lungs bisected, with half being homogenized for viral quantitation and the other half being inflated with formalin for histological examination.

On day 12, five animals from each group were sacrificed, their lungs bisected, with half being homogenized for viral quantitation and the other half being inflated with formalin for histological examination.

On day 14, five animals from each group were sacrificed, their lungs bisected, with half being homogenized for viral quantitation and the other half being inflated with formalin for histological examination.

Figure 4A:
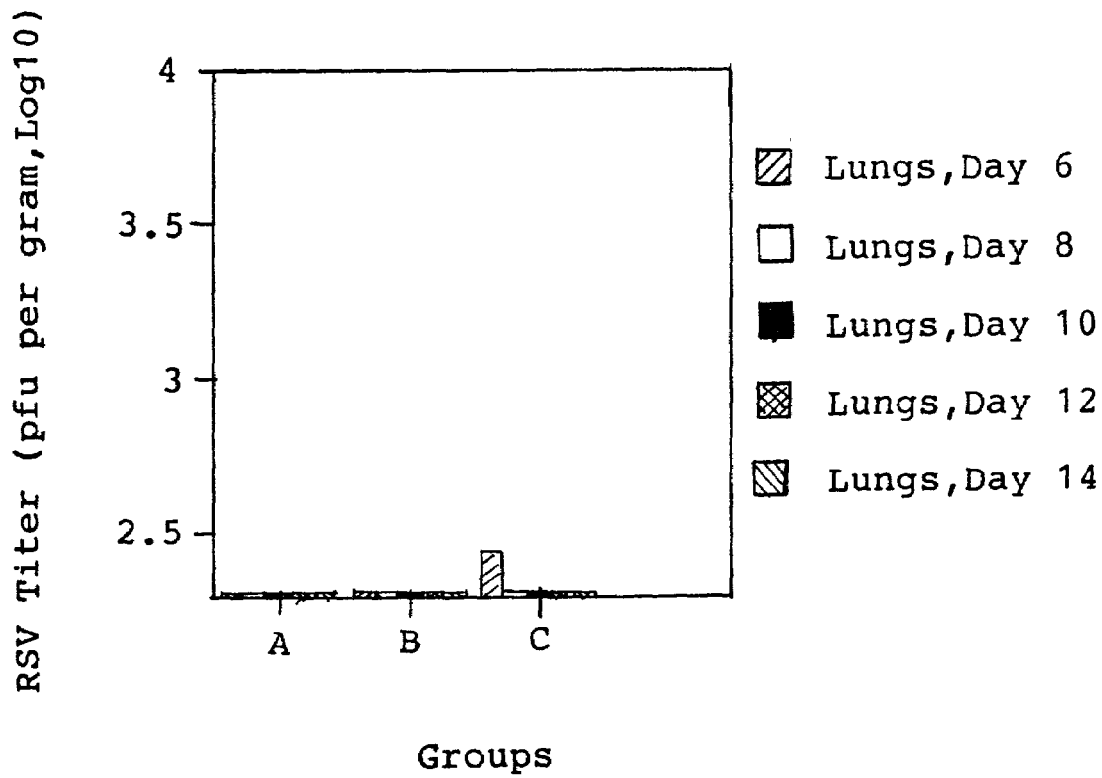
FIG. 4 shows the results of antibody/steroid combination therapy on RSV pneumonia in cotton rats as described in Example 2. Panel A shows the results for virus titer for groups 1–3, panel B shows the results for virus titer for groups 4–6, and panel C shows the results for composite pathology score. These data indicate a lack of rebound pathology following systemic combination therapy.
Figure 4B:
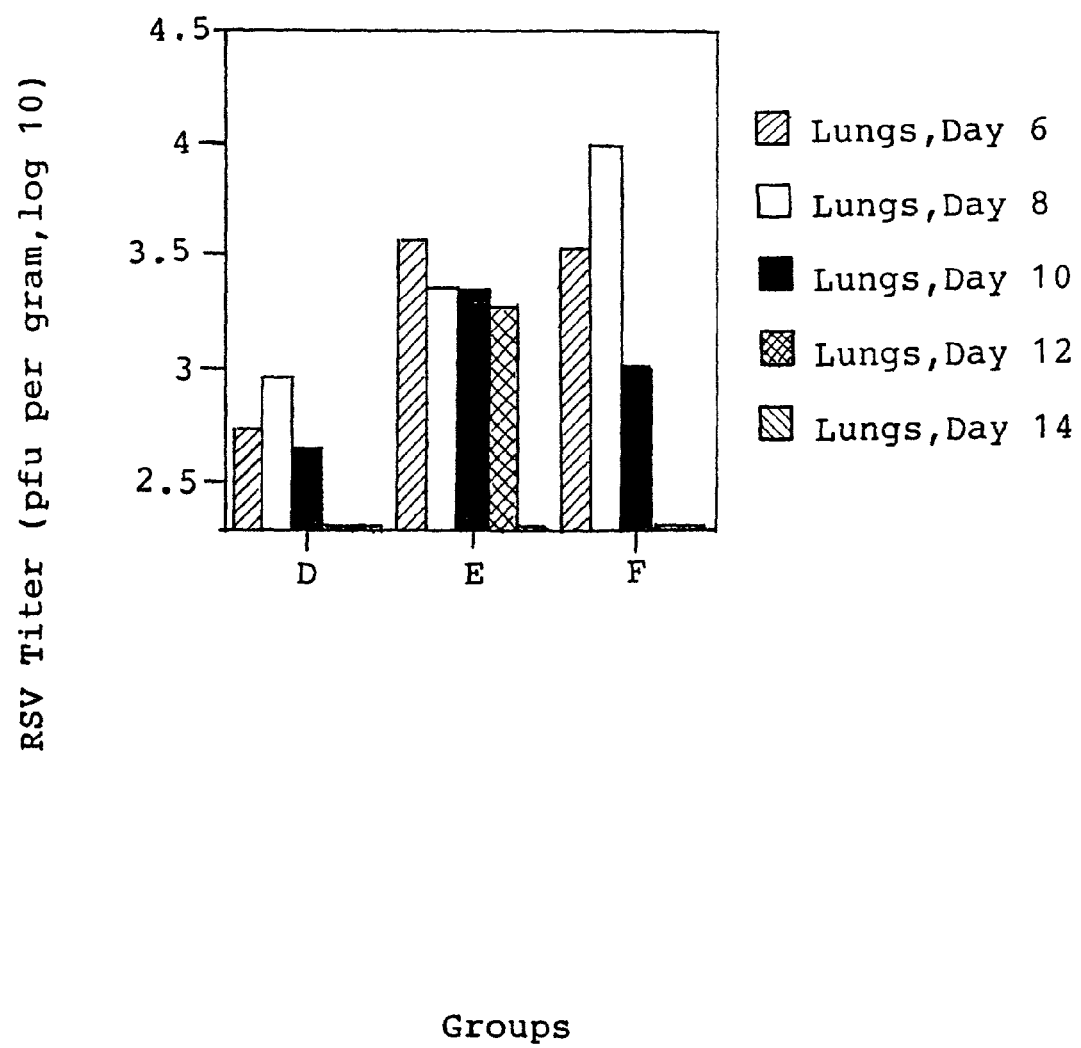
Figure 6A:
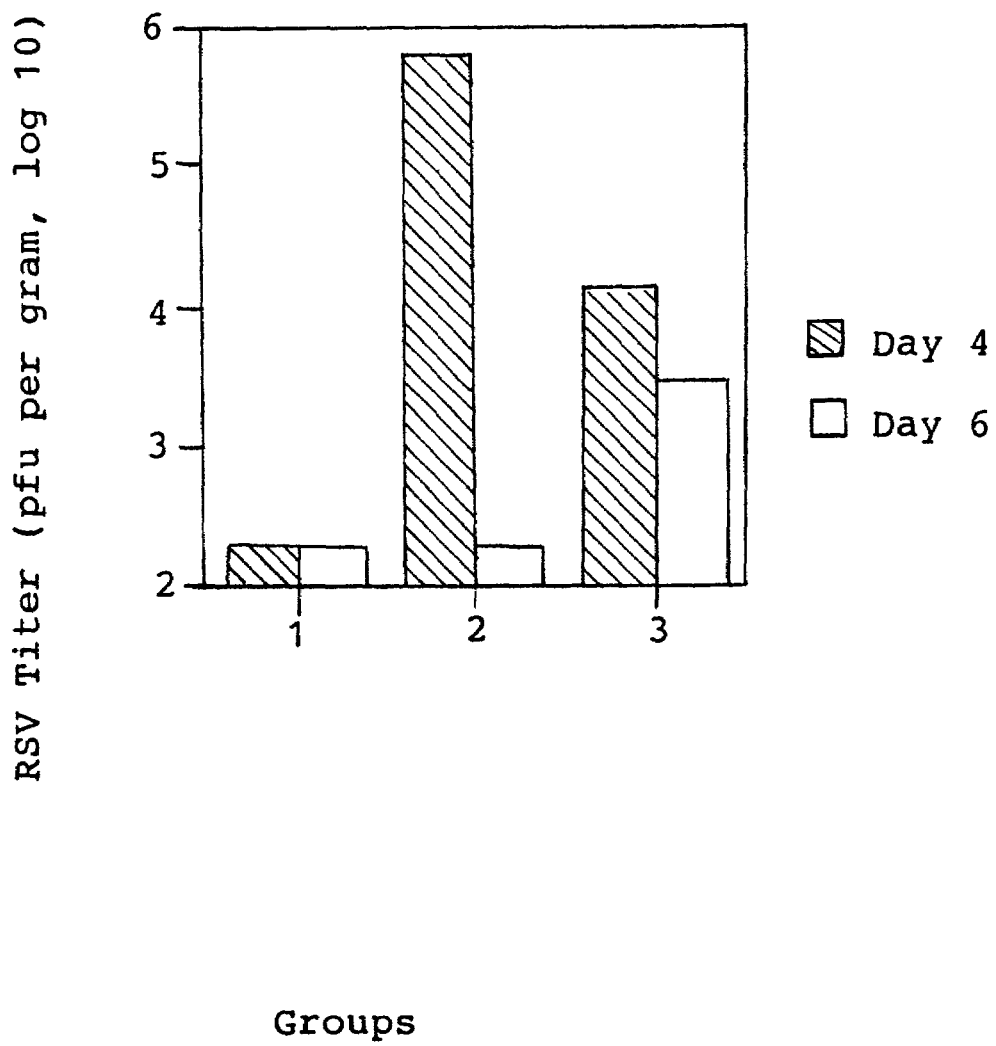
FIG. 6 shows effects of combined antibody/steroid therapy on mRNA levels in cotton rats with RSV pneumonia. Panel A shows virus titer and panel B shows pathology score for reference purposes. Panels C through G show mRNA levels.
Figure 6B:
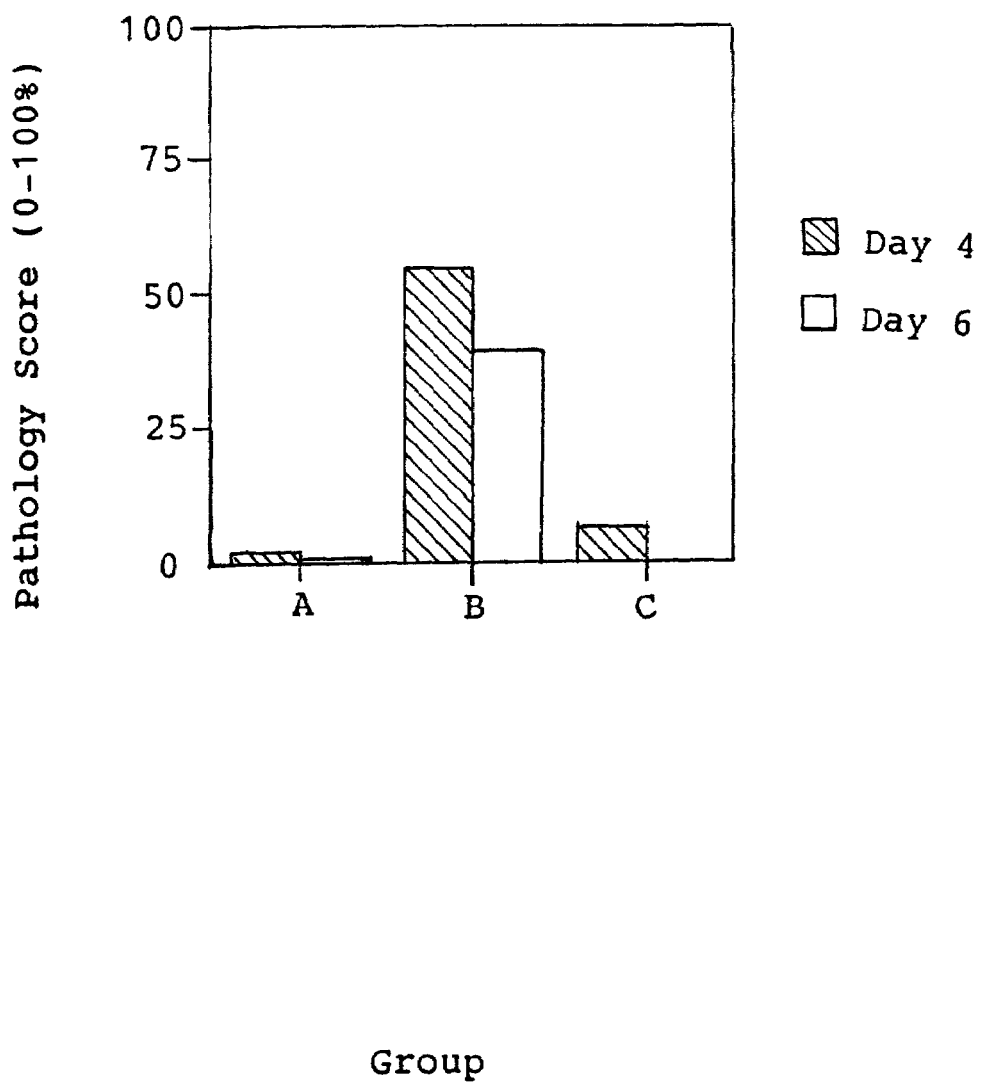
Figure 6C:
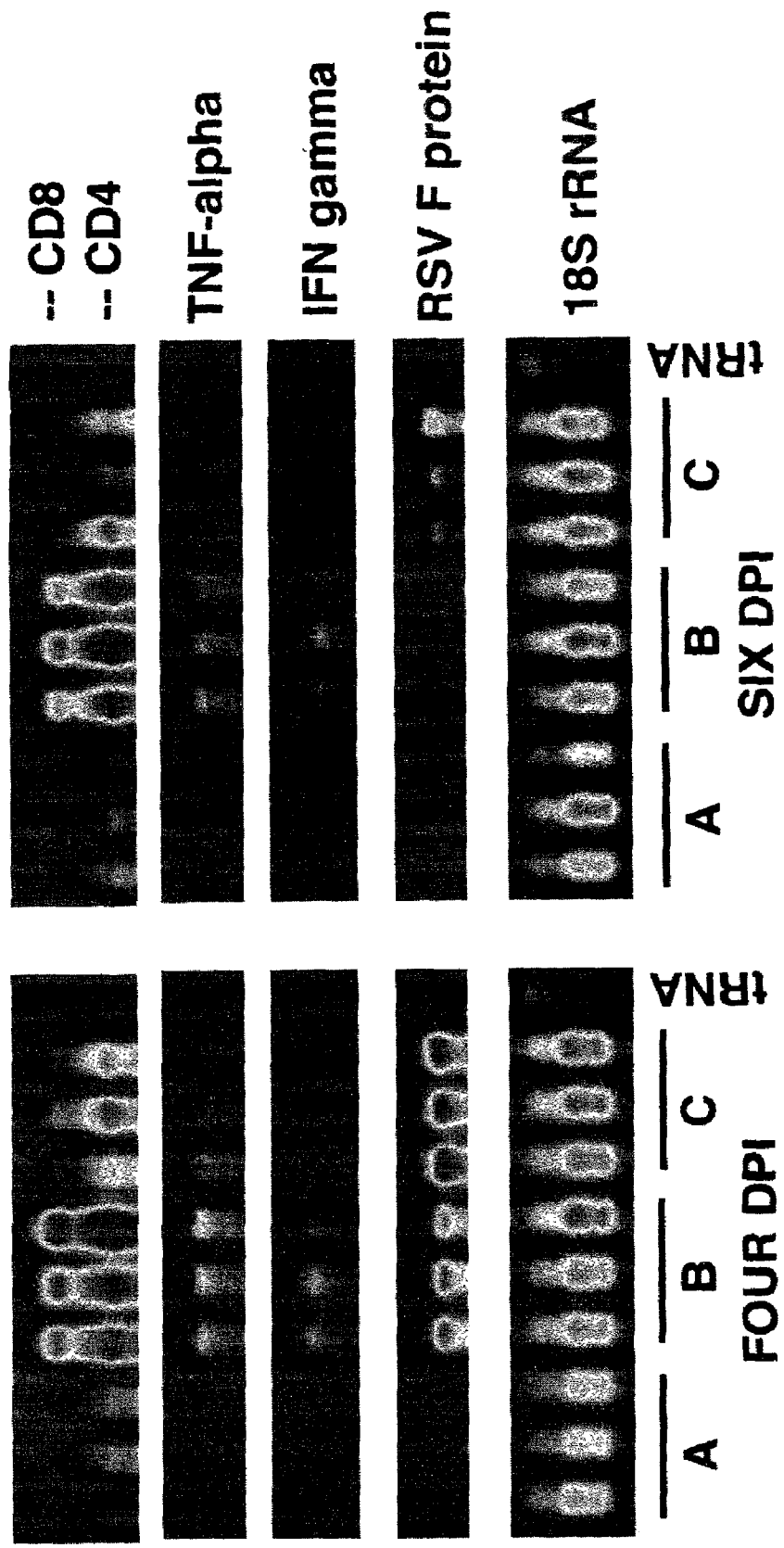
Figure 6D:
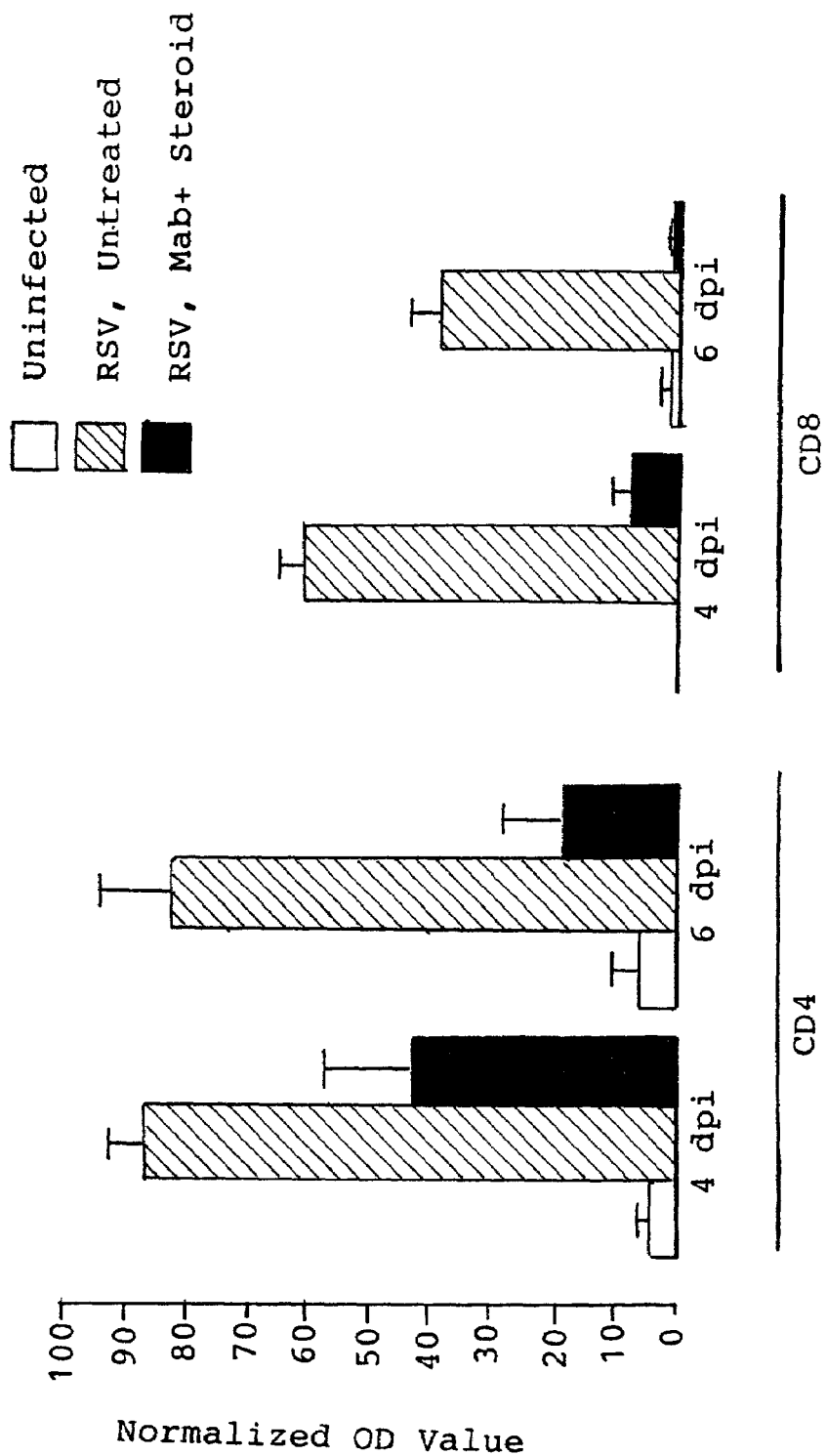
Figure 6F:
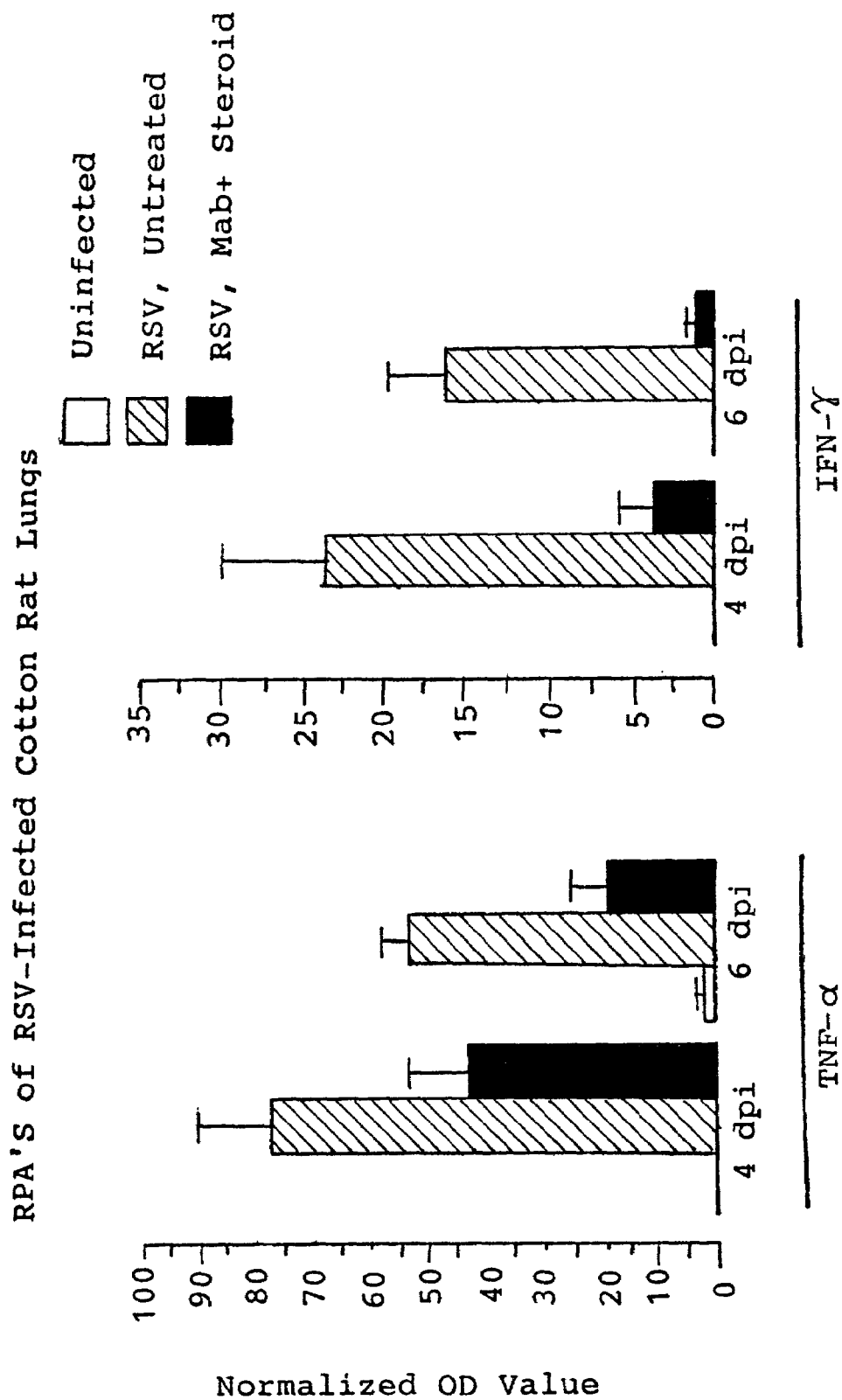
Figure 6G:
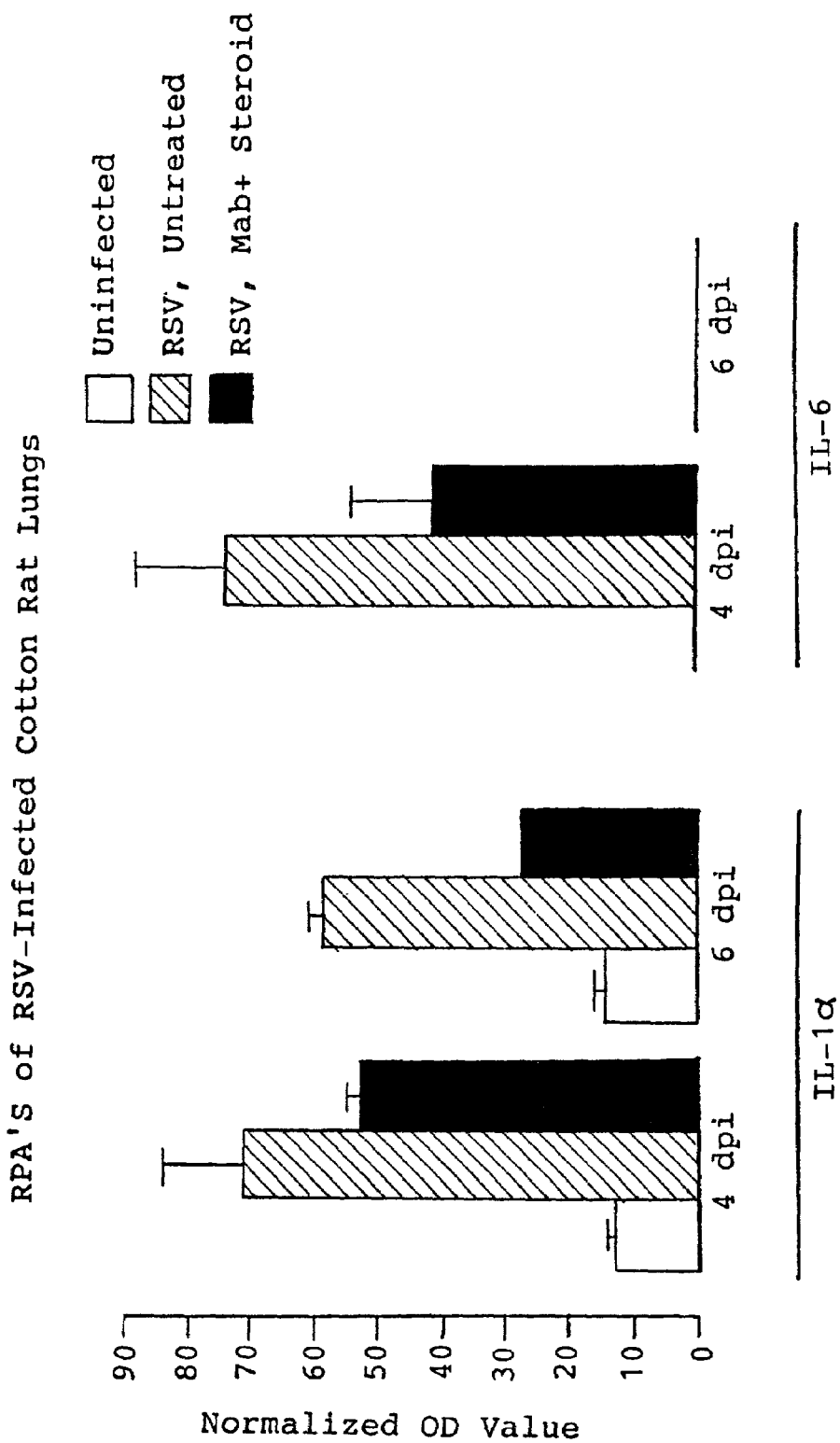

Results of these experiments are shown graphically in FIG. 4 (panels A–C). FIG. 4(a) shows the results of RSV titer in rats from group A–C. FIG. 2(b) shows the results of RSV titer for groups D–F. FIG. 4(c) shows a composite pathology score.

It has been reported in the literature [see: Prince and Porter, J. Infect. Dis., 173:598–608 (1996)] for combined therapy of PIV that short term therapy (days 3, 4, and 5) resulted in permanent clearance of infectious virus but pulmonary pathology "rebounded" after day 6. When therapy was continued through day 8 there was no rebound of pathology. However, those results involve topically administered antibody and corticosteroid. In the present experiments, both were administered systemically and show clearly the absence of a rebound effect after short duration therapy (days 3, 4, and 5).

EXAMPLE 3

The following procedure was performed using inbred cotton rats (Sigmodon hispidus). On day 0, young adult cotton rats were divided into 8 groups of 4 animals each (total: 32 animals). Identification of each group in terms of treatment was as follows:

| Group | Treatment | |
|---|---|---|
| A | uninfected/untreated | |
| B | RSV/untreated | |
| C | RSV/antibody | (15 mg/kg) i.m. |
| D | RSV/triamcinolone plus antibody (daily as one dose) | (16 mg/kg) i.m. |
| E | RSV/solumedrol plus antibody (Medrol given as | (4 mg/kg) i.p./ 1 mg/kg Q 6 hours) |
| F | RSV/solumedrol plus antibody (Medrol given as | (8 mg/kg) i.p./ 1 mg/kg Q 6 hours) |
| G | RSV/dexamethasone plus antibody (Daily as one dose) | (0.6 mg/kg) i.p./ |
| H | RSV/dexamethasone plus antibody (Daily as one dose) | (1.2 mg/kg) i.p./ |

In each case (Groups B–H), approximately $10^{6.5}$ plaque forming units (pfu) of respiratory syncytial virus (RSV/Long) was administered intranasally in a volume of 100 μl.

On day 3, treatment began as described above for each of the groups. The animals were each weighed and treated according to the indicated regimen. Antibody was palivizumab wherein 15 mg/kg was the dose used in each case. All dosages are given as mg per kg of body weight.

On day 4, animals in groups D through H were treated as described for day 3 but no additional antibody was given.

On day 5, animals in groups D through H were treated as on day 5 (again with no additional antibody).

On day 6, all animals were sacrificed. Lungs from all of the animals were inflated with formalin for histological examination.

The results of this experiment are summarized in FIG. 5 for arithmetic mean pathology scores. This experiment compares the efficacy of triamcinolone, solumedrol and dexamethasone, with the latter two given via routes and schedules commonly used in pediatrics. The higher dose of solumedrol (8 mg/kg/day) worked almost as well as triamcinolone but neither dose of dexamethasone worked as well (although it did reduce pulmonary pathology compared to untreated animals) and therefore solumedrol represents a potential candidate for clinical trials.

EXAMPLE 4

The following procedure was performed using inbred cotton rats (*Sigmodon hispidus*). On day 0, young adult cotton rats were divided into 3 groups of 6 animals each (total: 32 animals). Identification of each group in terms of treatment was as follows:

| Group | Treatment | |
|---|---|---|
| A | uninfected/untreated | |
| B | RSV/untreated | |
| C | RSV/triamcinolone plus antibody (daily as one dose) | (16 mg/kg) i.m. |

In each case (Groups B and C), approximately $10^{6.5}$ plaque forming units (pfu) of respiratory syncytial virus (RSV/Long) was administered intranasally in a volume of 100 μl.

On day 3, treatment began as described above for each of the groups. The animals were each weighed and treated according to the indicated regimen. Antibody was palivizumab wherein 15 mg/kg was the dose used in each case. All dosages are given as mg per kg of body weight. Treatment with antibody and steroid was intramuscular (i.m.).

On day 4, three animals from each group were sacrificed and their lungs trisected as follows: two left lobes were inflated with formalin for histology, 3 right lobes were treated by removing the top lobe for RNA analysis while the remaining lobes were homogenized for virus titration. The remaining animals in group 3 were treated with triamcinolone as on day 3 but not with any antibody.

On day 5, animals in group C were treated as on day 4 (again with no additional antibody).

On day 6, all remaining animals were sacrificed. Lungs from all of the animals were processed as described for day 3.

Results of this experiment are summarized in FIG. 6. Messenger RNA was measured in two cell types: CD4 and CD8, RSV F protein and four cytokines (TNF-α, IFN-γ, IL-1-α, and IL-6). [TNF=tumor necrosis factor, IFN=interferon, IL=interleukin] Results show that combined therapy significantly reduced the mRNA levels of both cell markers (CD4 and CD8) and all four cytokines. However, the level of mRNA for RSV F protein actually increased, despite the absence of infectious virus.

EXAMPLE 5

Twenty eight (28) cotton rats (CRs) were infected intranasally with 6.5 logs of RSV (as 0.1 ml of inoculum), leading to dramatic lung pathology 6 days post-infection (PI). On day 3 PI (the peak for viral infection), 7 groups of 4 animals received one of the following: no therapy, or intramuscular (i.m.) MAb (15 mg/kg) (MAb=palivizumab) i.m. triamcinolone (TRI;Steris Laboratories, Phoenix, Ariz.) at 16 mg/kg and MAb; i.p. methylprednisolone (MED; Solu-Medrol® Pharmacia and Upjohn, Kalamazoo, Mich.) 4 mg/kg and MAb; i.p. MED at 8 mg/kg and MAb; i.p. dexamethasone (DEX; Elkins-Sinn, Cherry Hill, N.J.) 0.6 mg/kg and MAb; or i.p. DEX 1.2 mg/kg and MAb (TRI and DEX once daily, MED divided into every 6 hours). All glucocorticoids were repeated on days 4 and 5. The dose, frequency and route of administration of dexamethasone and methylprednisolone were extrapolated from human use recommendations.

On day 6, all groups (including 4 uninfected CRs were sacrificed (in general by carbon dioxide asphyxiation). For pathology, tissues were inflated and formalin fixed and coronal paraffin sections were cut at 4 μm thickness. Lung tissue slides scored on a 0 (normal) to 100 (marked pathology) severity scale, for bronchiolitis, alveolitis, and interstitial pneumonia.

On day 6, untreated RSV infection showed significant components of peribronchiolitis, interstitial pneumonia and alveolitis with a predominating mononuclear infiltrate. Little or no improvement was apparent for tissues on day 6 following treatment with palivizumab alone on day 3. RSV infection on day 6, after treatment with palivizumab on day 3 and methylprednisolone on days 3, 4 and 5 showed a reduction in inflammatory infiltrates to a level near that of the uninfected control. All such tissues were observed at 64X with hematoxylin and eosin staining. Results are shown graphically in FIG. 7A and summarized as follows in terms of pathology score (0 to 100).

TABLE 1

| Therapy | | Bronchiolitis | Alveolitis | Interstitial Pneumonia |
|---|---|---|---|---|
| No infection | | 1 | 2 | 2 |
| RSV infected only | | 88 | 48 | 60 |
| MAb only | | 75 | 38 | 49 |
| | TRI + MAb | 3 | 5 | 6 |
| 4 mg | MED + MAb | 16 | 6 | 8 |
| 8 mg | MED + MAb | 9 | 6 | 11 |
| 0.6 mg | DEX + MAb | 23 | 7 | 17 |
| 1.2 mg | DEX + MAb | 34 | 13 | 20 |

Palivizumab treatment alone did not reduce pathology. The combination of this MAb with TRI and MED reduced pathology to near baseline levels.

EXAMPLE 6

Four groups of 20 cotton rats each were infected intranasally with 106.5 phu of RSV long. On the third day post-infection animals in three of the groups received one dose of intramuscular palivizumab (15 mg/kg) and concurrent glucocorticoid therapy on days 3, 4, and 5, in the following doses: triamcinolone acetonide (16 mg/kg im once daily); methylprednisolone (4 mg/kg divided as 1 mg/kg every 6 hours), or dexamethasone (0.6 mg/kg ip once daily). Animals were sacrificed on days 6, 8, 10, 12 and 14 post-infection for viral titration and histopathology.

Lung tissue homogenized in 10 parts Hanks' balanced salt solution supplemented with 0.218 M sucrose, 4.4 mM glutamate, 3.8 mM $KH_2PO_4$, and 7.2 mM $KH_2PO_4$ and stored at $-70°$ C. for viral titration. Tissue was treated for pathology as already described. Results are shown in FIG. 7B.

Figure 7B:
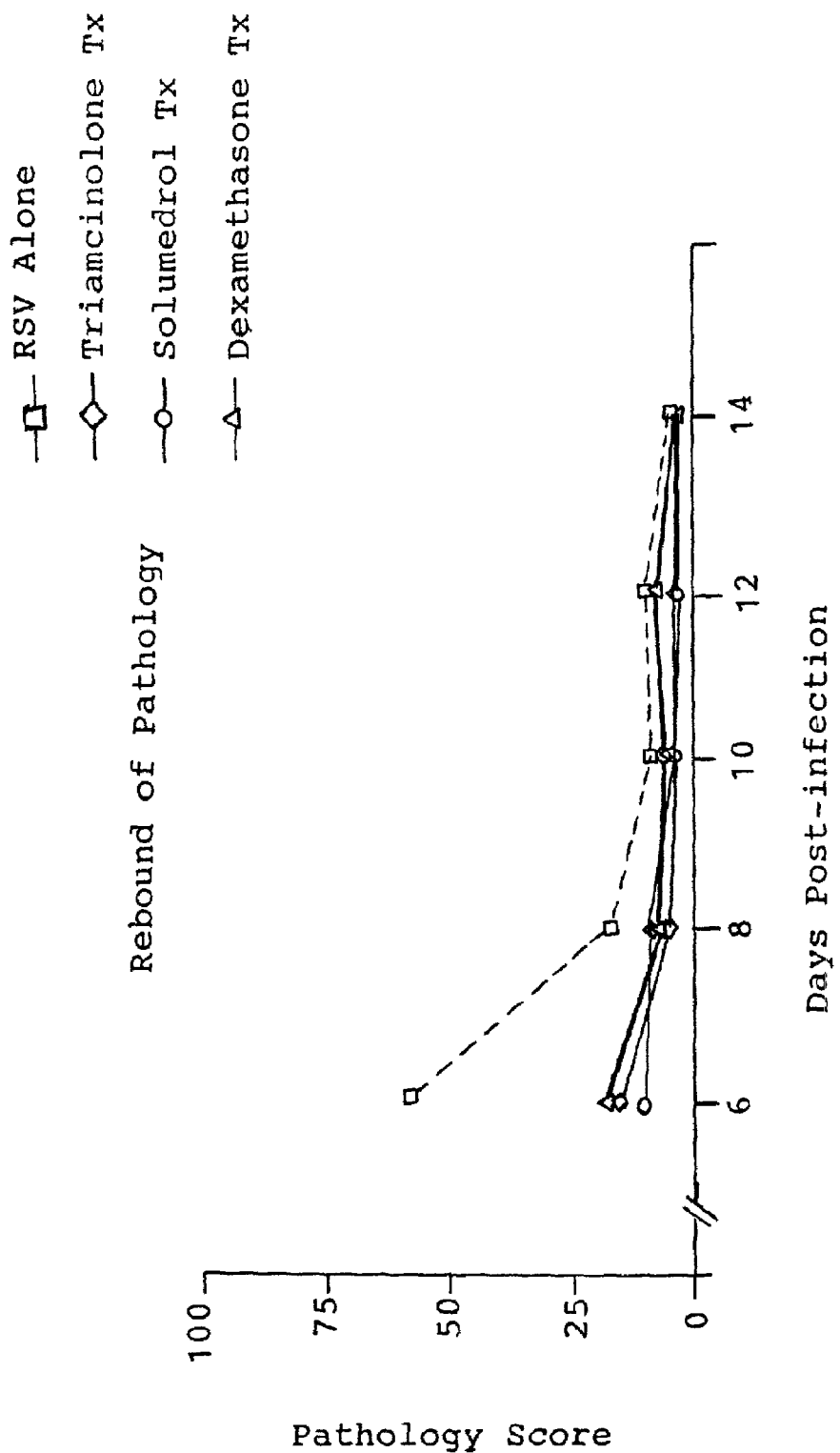
FIG. 7 shows pulmonary pathology after treatment with antibody and steroids.

Inflammation following RSV infection was significant on day 6 post-infection but slowly abated over the following 8 days (as shown in FIG. 7B). All three glucocorticoid treated groups had greater reductions in pathology but no group had rebound of histopathology over the two week period. On day 6, $10^{6.5}$ pfu of RSV per gram was recovered from the lungs of untreated animals while only $10^3$ pfu/g was recovered from the lungs of triamcinolone/palivizumab treated animals on days 6 and 8 post-infection. No further viral replication was detected in any groups during the remainder of the experiment. This low level of viral replication, with no signs of rebound, eliminated the need for comparative statistical analysis of viral titrations.

What is claimed is:

1. A method of treating respiratory syncytial virus infection (RSV) in a patient afflicted therewith comprising administering to said patient a therapeutically effective regimen of an anti-RSV antibody and a steroid wherein said regimen is administered systemically.

2. The method of claim 1 wherein the steroid is a corticosteroid.

3. The method of claim 2 wherein said corticosteroid is selected from the group consisting of cortisone, hydrocortisone, prednisone, prednisolone, methylprednisolone, triamcinolone, betamethasone, beclamethasone and dexamethasone.

4. The method of claim 1 wherein the anti-viral antibody is administered in a dosage of 5 to 20 mg/kg body weight.

5. The method of claim 1 wherein the anti-viral antibody is MEDI-493 (palivizumab).

6. The method of claim 1 wherein said steroid is administered in the dosage range is 0.5 mg to 50 mg per kg body weight.

7. The method of claim 1 wherein said steroid is administered in a dosage of 10 µg to 1 gram per kg body weight.

8. The method of claim 1 wherein said antibody and said steroid are administered contemporaneously.

9. The method of claim 1 wherein the antibody is administered prior to administering the steroid.

10. The method of claim 1 wherein the steroid is administered prior to administering the antibody.

* * * * *